(12) United States Patent
Kim et al.

(10) Patent No.: US 11,339,167 B2
(45) Date of Patent: May 24, 2022

(54) SUBSTITUTED PIPERIDINES AS KINASE INHIBITORS

(71) Applicant: Daewoong Pharmaceutical Co., Ltd., Gyeonggi-do (KR)

(72) Inventors: In Woo Kim, Seoul (KR); Sun Ah Jun, Gyeonggi-do (KR); Nam Youn Kim, Gyeonggi-do (KR); Jun Hee Lee, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 67 days.

(21) Appl. No.: 16/770,638

(22) PCT Filed: Dec. 28, 2018

(86) PCT No.: PCT/KR2018/016814
§ 371 (c)(1),
(2) Date: Jun. 8, 2020

(87) PCT Pub. No.: WO2019/132562
PCT Pub. Date: Jul. 4, 2019

(65) Prior Publication Data
US 2020/0308177 A1 Oct. 1, 2020

(30) Foreign Application Priority Data
Dec. 28, 2017 (KR) .................. 10-2017-0183061

(51) Int. Cl.
*A61K 31/519* (2006.01)
*C07D 487/04* (2006.01)

(52) U.S. Cl.
CPC .................. *C07D 487/04* (2013.01)

(58) Field of Classification Search
CPC ..................... A61K 31/519; C07D 487/04
USPC ......................... 514/265.1; 544/280
See application file for complete search history.

(56) References Cited

U.S. PATENT DOCUMENTS

| | | |
|---|---|---|
| 2003/0073719 A1 | 4/2003 | Wilcox et al. |
| 2009/0298823 A1 | 12/2009 | Song et al. |
| 2012/0094999 A1 | 4/2012 | Gray et al. |
| 2013/0029944 A1 | 1/2013 | Song et al. |
| 2013/0079324 A1 | 3/2013 | Cheng et al. |
| 2014/0200207 A1 | 7/2014 | Calabrese et al. |
| 2015/0158864 A1 | 6/2015 | Thorarensen et al. |
| 2015/0203502 A1 | 7/2015 | Cheng et al. |
| 2016/0002243 A1 | 1/2016 | De Vicente Fidalgo et al. |
| 2016/0229865 A1 | 8/2016 | Liu et al. |
| 2017/0247372 A1 | 8/2017 | Thorarensen et al. |
| 2018/0051036 A1 | 2/2018 | Liu et al. |
| 2019/0040065 A1 | 2/2019 | Gray et al. |
| 2020/0317673 A1 | 10/2020 | Kim et al. |

FOREIGN PATENT DOCUMENTS

| | | |
|---|---|---|
| CA | 2803056 A1 | 12/2011 |
| CL | 2008000762 A1 | 7/2008 |
| CL | 2014000566 A1 | 10/2014 |
| CL | 2015001990 A1 | 1/2016 |
| CL | 2016001216 A1 | 1/2017 |
| CL | 2018003511 A1 | 4/2019 |
| CL | 2020001749 A1 | 11/2020 |
| CL | 2020001754 A1 | 11/2020 |
| CN | 102066338 A | 5/2011 |

(Continued)

OTHER PUBLICATIONS

Jordan, V. C. Nature Reviews: Drug Discovery, 2, 2003, 205-213.*
Hackam, et al. JAMA, 296(14), 2006, 1731-1732.*
Zhou et al., "Discovery of Selective Irreversible Inhibitors for EGFR-T790M", Bioorganic & Medicinal Chemistry Letters, vol. 21, 2011, pp. 638-643.
D'Aura et al., "Tyrosine Kinases as Targets for the Treatment of Rheumatoid Arthritis", Nature Reviews Rheumatology, vol. 5, Jun. 2009, pp. 317-324.
Peter Norman, "Selective JAK Inhibitors in Development for Rheumatoid Arthritis", Expert Opin Investig Drugs, vol. 8, Aug. 23, 2014, 11 pages.

(Continued)

*Primary Examiner* — Douglas M Willis
(74) *Attorney, Agent, or Firm* — Marshall, Gerstein & Borun LLP

(57) ABSTRACT

The present invention relates to a compound represented by the following Chemical Formula 1, or a pharmaceutically acceptable salt, stereoisomer, or tautomer thereof, and the compound according to the present invention can be usefully used for the prevention or treatment of diseases which are associated with kinase inhibitory actions:

Chemical Formula 1

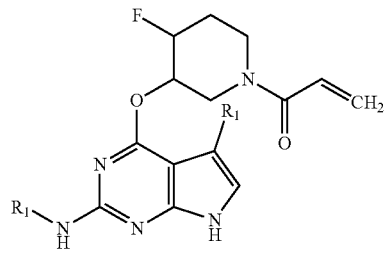

wherein:
$R_1$ is pyrazolyl, isooxazolyl, isothiazolyl, phenyl, or benzothiazolyl, wherein the pyrazolyl, isoxazolyl, isothiazolyl, phenyl, or benzothiazolyl is optionally substituted with one $R_a$ substituent;
$R_2$ is H, halogen, CN, or $C_{1-5}$ alkyl; and
$R_a$ is $C_{1-5}$ alkyl, $C_{1-5}$ haloalkyl, $C_{1-5}$ hydroxyalkyl, $C_{3-6}$ cycloalkyl, tetrahydropyranyl, piperidinyl, or morpholino.

9 Claims, No Drawings

(56) References Cited

FOREIGN PATENT DOCUMENTS

| | | | |
|---|---|---|---|
| CN | 102482277 A | 5/2012 | |
| CN | 103748096 A | 4/2014 | |
| CN | 103814030 A | 5/2014 | |
| CN | 104311573 A | 1/2015 | |
| CN | 105073750 A | 11/2015 | |
| CN | 105732637 A | 7/2016 | |
| CN | 106061973 A | 10/2016 | |
| EP | 3202403 A1 | 8/2017 | |
| JP | 2013529630 A | 7/2013 | |
| JP | 2015524468 A | 8/2015 | |
| KR | 2012-0047208 A | 5/2012 | |
| KR | 2014-0059246 A | 5/2014 | |
| KR | 2016-0054014 A | 5/2016 | |
| KR | 2016-0092012 A | 8/2016 | |
| KR | 20180137057 A | 12/2018 | |
| WO | WO-02/096909 A1 | 12/2002 | |
| WO | WO-2009/026107 A1 | 2/2009 | |
| WO | WO-2010/009342 A2 | 1/2010 | |
| WO | WO-2010129053 A2 | 11/2010 | |
| WO | WO-2014025486 A1 | 2/2014 | |
| WO | WO-2015083028 A1 | 6/2015 | |
| WO | WO-2016/000615 A1 | 1/2016 | |
| WO | WO-2017106771 A1 | 6/2017 | |
| WO | WO-2018/004306 A1 | 1/2018 | |
| WO | WO-2019132560 A1 | 7/2019 | |
| WO | WO-2019132561 A1 | 7/2019 | |
| WO | WO-2019132562 A1 * | 7/2019 | ............. A61P 37/00 |

OTHER PUBLICATIONS

Whang et al., "Bruton's Tyrosine Kinase Inhibitors for the Treatment of Rheumatoid Arthritis", Drug Discovery Today, vol. 8, Aug. 19, 2014, 8 pages.

Search Report and Written Opinion in Internaitonal Application No. PCT/KR2018/016814 dated Apr. 8, 2019, 16 pages.

Office Action in SG Patent Application No. 11202004917U dated Apr. 29, 2021, 10 pages.

Office Action in CL Patent Application No. 1752-2020 dated May 3, 2021, 20 pages.

Office Action in EP Patent Application No. 18896304.5 dated May 11, 2021, 8 pages.

Office Action in JP Patent Application No. 2020-532893 dated Jun. 15, 2021.

Planken, S. et al. "Discovery of N-((3 R, 4 R)-4-Fluoro-1-(6-((3-methoxy-1-methyl-1 H-pyrazol-4-yl) amino)-9-methyl-9 H-purin-2-yl) pyrrolidine-3-yl) acrylamide (PF-06747775) Through Structure-Based Drug Design: A High Affinity Irreversible Inhibitor Targeting Oncogenic EGFR Mutants with Selectivity over Wild-Type EGFR." *Journal of Medicinal Chemistry* 60, No. 7 (2017): 3002-3019.

Office Action in CN Application No. 201880084457.1 dated Mar. 25, 2022, 10 pages.

\* cited by examiner

SUBSTITUTED PIPERIDINES AS KINASE INHIBITORS

TECHNICAL FIELD

The present invention relates to an oxy-fluoropiperidine derivative having kinase inhibitory activity, a process for preparing the same and use thereof.

BACKGROUND OF ART

Protein kinase is an enzyme that catalyzes phosphorylation of specific residues of other proteins, and plays an important role in signal-transduction pathways that transduce extracellular signals to the nucleus. Further, it is involved in various diseases in vivo. In the onset or development of inflammatory disease, autoimmune disease, proliferative disease or hyperproliferative disease, and/or immunity mediated disease, there is various evidence that T-cells (or T-lymphocytes) and B-cells (or B-lymphocytes) play an important role.

Janus kinase (hereinafter referred to as "JAK") is a cytoplasmic protein tyrosine kinase that plays pivotal roles in regulating cell function in the lympho-hematopoietic system. Cytokines are known to play an important role in regulating inflammation, immunity and normal cell function, and JAK activates STAT (Signal Transducer and Activators of Transcription) proteins through tyrosine phosphorylation to provide rapid signaling pathways to cytokines. JAK/STAT signaling is known to be associated with allergies, asthma, autoimmune diseases (e.g., transplant rejection, rheumatoid arthritis, amyotrophic lateral sclerosis, multiple sclerosis etc.), solid cancers, blood cancers (e.g., leukemia, lymphoma and so on).

The JAK family is classified into four members: JAK 1, JAK 2, JAK 3, and TYK 2. Members of the JAK family pair with each other to mediate signals from a variety of cytokines. It includes JAK2 and JAK1 associated with hematopoietic growth factor signaling, and a combination of TYK2 and JAK2 is important for interferon signaling and contributes to host tolerance. JAK2 can induce anemia, thrombocytopenia, leukopenia, especially when it is involved in the hematopoietic growth factor signaling and causes excessive inhibition.

The expression of JAK1, JAK2, and TYK2 was found to be widely distributed, whereas the expression of JAK3 was restricted to lymphocytes and is associated with signaling for the common gamma chains, members of IL-2, IL-4, IL-7, IL-9, IL-15 and IL-21 receptors, particularly the common gamma chain of the IL-2 family. As soon as the cytokine is bound, the receptor carries adjacent JAK3 nearby, which induces autophosphorylation of the β-chain C-terminus. As a result, it causes activation of the STAT protein, which is an important step in retransmitting the signal to the nucleus. JAK3 controls the signal pathways of various cytokines through this process. This makes JAK3 as an attractive target for immunosuppression.

B cells play an important role in the development of autoimmune and/or inflammatory diseases. Protein-based therapeutic agents that reduce B cells, for example Rituxan, are effective in autoantibody-induced inflammatory diseases such as rheumatoid arthritis. Thus, protein kinase inhibitors that play a role in B cell activation are useful therapeutic agents for the treatment of B cell-mediated diseases, for example, for the production of autoantibodies.

Signal transduction through B cell receptor (BCR) regulates various B cell responses, including proliferation and differentiation into mature antibody-producing cells. BCR is an important regulatory element of B cell activity, and abnormal signal transduction can cause the formation of pathogenic autoantibodies leading to a plurality of autoimmune and/or inflammatory diseases and the proliferation of deregulated B cell.

Bruton tyrosine kinase (hereinafter, referred to as "BTK") is an important regulator of the development, activation, signaling and survival of B-cells. BTK is involved in signal transduction pathways initiated by binding various extracellular ligands to their cell surface receptors. Following ligation of the B cell antigen receptor (BCR), the activity of BTK by the coincident action of the protein tyrosine kinases Lyn and Syk is required for the induction of the phospholipase C-v2-mediated calcium mobilization. Therefore, inhibition of BTK can be a useful therapeutic approach in blocking the onset process of B-cell mediated diseases.

As mentioned above, Janus kinase and TEC-based kinases play an important role in the activation of T-cells and/or B-cells involved in the development of inflammatory diseases, autoimmune diseases, proliferative diseases or hyperproliferative diseases, and immunity mediated diseases. Therefore, the development of substances that effectively inhibit these diseases can be useful as a related therapeutic agent. Specific examples of the diseases which can be treated and prevented include cancer, transplant rejection, multiple sclerosis, rheumatoid arthritis, psoriatic arthritis, psoriasis, asthma, allergic dermatitis, atopic dermatitis, eczema, type I diabetes, diabetic complication, ulcerative colitis, Crohns disease, autoimmune thyroid disorder, systemic depilation, Sjogrens syndrome and the like.

JAK3 kinase inhibitor, tofacitinib (CP-690550) (Pfizer Inc.) is currently approved and marketed for the treatment of rheumatoid arthritis. In addition, a BTK kinase inhibitor, ibrutinib (PCI-32765) (Pharmacyclics) is in a clinical stage, but severe side effects such as skin rash and diarrhea have been reported in clinical cases. Thus, there is a need to develop a more stable and effective substance that inhibits JAK and/or BTK (see, Nat Rev Rheumatol. 2009 Jun. 5(6) 317-24; Expert Opin Investig Drugs. 2014 Aug. 23(8) 1067-77; Drug Discov Today 2014 Aug. 19(8) 1200-4; WO2002/096909; WO2010-009342).

Therefore, the present inventors have found a new oxy-fluoropiperidine derivative having an excellent inhibitory activity as a kinase inhibitor, thereby completing the present invention.

DETAILED DESCRIPTION OF THE INVENTION

Technical Problem

It is an object of the present invention to provide an oxy-fluoropiperidine derivative having an inhibitory ability against kinase, particularly tyrosine kinase, a process for preparing the same and use thereof.

It is another object of the present invention to provide a pharmaceutical composition comprising the oxy-fluoropiperidine derivative as an active ingredient.

Technical Solution

In order to achieve the above objects, a compound represented by the following Chemical Formula 1, or a pharmaceutically acceptable salt thereof is provided herein:

[Chemical Formula 1]

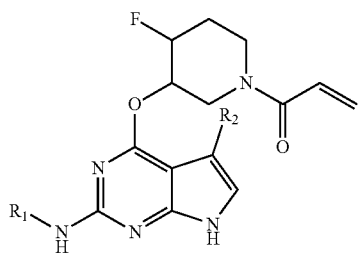

wherein, in Chemical Formula 1, $R_1$ is pyrazolyl, isoaxazolyl; isothiazolyl; phenyl; or benzothiazolyl, where $R_1$ is unsubstituted or substituted with $R_a$, $R_a$ is $C_{1-5}$ alkyl, $C_{1-5}$ haloalkyl, $C_{3-6}$ cycloalkyl, $C_{1-5}$ hydroxyalkyl, morpholino, tetrahydropyranyl, or piperidinyl, and $R_2$ is hydrogen, $C_{1-5}$ alkyl, halogen, or cyano.

Preferably, R is methyl, ethyl, propyl, isopropyl, butyl, isobutyl, pentyl, isopentyl, neopentyl, fluoromethyl, difluoromethyl, trifluoromethyl, 2-fluoroethyl, 2,2-difluoroethyl, 2,2,2-trifluoroethyl, cyclopropyl, cyclobutyl; cyclopentyl, cyclohexyl, hydroxymethyl; 2-hydroxyethyl, morpholino, tetrahydropyranyl, or piperidinyl, Preferably, $R_2$ is hydrogen, methyl, ethyl, propyl, isopropyl, butyl, isobutyl, pentyl, isopentyl, neopentyl, fluoro, chloro, bromo, or cyano.

Preferably, the Chemical Formula 1 is represented by the following Chemical Formula 1-1:

[Chemical Formula 1-1]

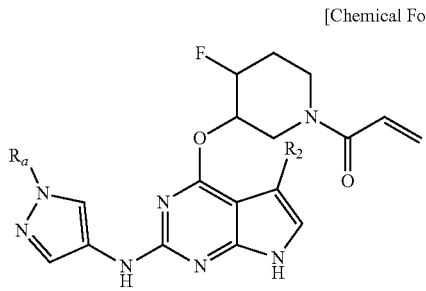

wherein, in Chemical Formula 1-1, $R_a$ and $R_2$ are as defined above.

Preferably, in the Chemical Formula 1-1, R is $C_{1-5}$ alkyl, $C_{1-5}$ haloalkyl, $C_{3-6}$ cycloalkyl, $C_{1-5}$ hydroxyalkyl, tetrahydropyranyl, or piperidinyl, and more preferably ethyl, 2,2-difluoroethyl, cyclopropyl, 2-hydroxyethyl; tetrahydropyranyl, or piperidinyl. Preferably, in the Chemical Formula 1-1, $R_2$ is hydrogen, $C_{1-5}$ alkyl, halogen, or cyano, and more preferably hydrogen, methyl, fluoro, chloro, or cyano.

Preferably, the Chemical Formula 1 is represented by the following Chemical Formula 1-2:

[Chemical Formula 1-2]

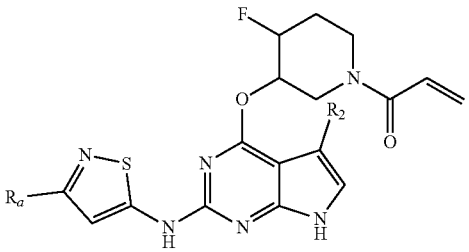

wherein, in Chemical Formula 1-2, $R_a$ and $R_2$ are as defined above.

Preferably, in the Chemical Formula 1-2, $R_a$ is $C_{1-5}$ alkyl, and more preferably methyl. Preferably, in the Chemical Formula 1-2, $R_2$ is hydrogen, or $C_{1-5}$ alkyl, and more preferably hydrogen or methyl, Typical examples of the compounds represented by the Chemical Formula 1 are as follows:

1) 1-(trans-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one,
2) 1-(trans-3-((2-((1-(2,2-difluoroethyl)-1H-pyrazol-4-yl)amino)-7H-pyrrolo[2,3-d]pyrimidin-4-yl)oxy)-4-fluoropiperidin-1-yl)prop-2-en-1-one,
3) 1-(trans-3-((2-(1-cyclopropyl-1H-pyrazol-4-ylamino)-7H-pyrrolo[2,3-d]pyrimidin-4-yloxy)-4-fluoropiperidin-1-yl)prop-2-en-1-one,
4) 1-(cis-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one,
5) 1-((3S,4R)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one,
6) 1-((3S,4R)-3-((2-((1-(2,2-difluoroethyl)-1H-pyrazol-4-yl)amino)-7H-pyrrolo[2,3-d]pyrimidin-4-yl)oxy)-4-fluoropiperidin-1-yl)prop-2-en-1-one,
7) 1-((3S,4R)-4-fluoro-3-((2-((3-methylisothiazol-5-yl)amino)-7H-pyrrolo[2,3-d]pyrimidin-4-yl)oxy)piperidin-1-yl)prop-2-en-1-one,
8) 1-((3S,4R)-3-((2-((1-cyclopropyl-1H-pyrazol-4-yl)amino)-7H-pyrrolo[2,3-d]pyrimidin-4-yl)oxy)-4-fluoropiperidin-1-yl)prop-2-en-1-one,
9) 1-(trans-3-((5-chloro-2-((1-ethyl-1H-pyrazol-4-yl)amino)-7H-pyrrolo[2,3-d]pyrimidin-4-yl)oxy)-4-fluoropiperidin-1-yl)prop-2-en-1-one,
10) 1-(trans-3-((5-chloro-2-((1-cyclopropyl-1H-pyrazol-4-yl)amino)-7H-pyrrolo[2,3-d]pyrimidin-4-yl)oxy)-4-fluoropiperidin-1-yl)prop-2-en-1-one,
11) 1-(trans-3-((5-chloro-2-((3-methyl isothiazol-5-yl)amino)-7H-pyrrolo[2,3-d]pyrimidin-4-yl)oxy)-4-fluoropiperidin-1-yl)prop-2-en-1-one,
12) 4-((trans-1-acryloyl-4-fluoropiperidin-3-yl)oxy)-2-((1-ethyl-1H-pyrazol-4-yl)amino)-7H-pyrrolo[2,3-d]pyrimidine-5-carbonitrile,
13) 4-((trans-1-acryloyl-4-fluoropiperidin-3-yl)oxy)-2-((1-cyclopropyl-1H-pyrazol-4-yl)amino)-7H-pyrrolo[2,3-d]pyrimidine-5-carbonitrile,
14) 4-((trans-1-acryloyl-4-fluoropiperidin-3-yl)oxy)-2-(1-(2,2-difluoroethyl)-1H-pyrazol-4-yl)amino)-7H-pyrrolo[2,3-d]pyrimidine-5-carbonitrile,
15) 1-(cis-3-((2-(1-ethyl-1H-pyrazol-4-yl)amino)-5-fluoro-7H-pyrrolo[2,3-d]pyrimidin-4-yl)oxy)-4-fluoropiperidin-1-yl)prop-2-en-1-one, 16) 1-(cis-3-((2((1-(2,2-difluoroethyl)-1H-pyrazol-4-yl) amino)-5-fluoro-7H-pyrrolo[2,3-d]pyrimidin-4-yl)oxy)-4-fluoropiperidin-1-yl)prop-2-en-1-one, 17) 1-(cis-3-((2-(1-ethyl-1H-pyrazol-4-yl)amino)-5-methyl-7H-pyrrolo[2,3-d]pyrimidin-4-yl)oxy)-4-fluoropiperidin-1-yl)prop-2-en-1-one, 18) 1-(cis-3-((2((1-(2,2-difluoroethyl)-1H-pyrazol-4-yl) amino)-5-methyl-7H-pyrrolo[2,3-d]pyrimidin-4-yl)oxy)-4-fluoropiperidin-1-yl)prop-2-en-1-one, 19) 1-((3S,4R)-3-((2-((1-ethyl-1H-pyrazol-4-yl)amino)-5-methyl-7H-pyrrolo[2,3-d]pyrimidin-4-yl)oxy)-4-fluoropiperidin-1-yl)prop-2-en-1-one, 20) 1-((3S,4R)-3-((2-((1-(2,2-difluoroethyl)-1H-pyrazol-4-yl)amino)-5-methyl-7H-pyrrolo[2,3-d]pyrimidin-4-yl) oxy)-4-fluoropiperidin-1-yl)prop-2-en-1-one, 21) 1-((3S,4R)-4-fluoro-3-((5-methyl-2-((3-methyl isothiazol-5-yl)amino)-7H-pyrrolo[2,3-d]pyrimidin-4-yl)oxy) piperidin-1-yl)prop-2-en-1-one, 22) 1-((3S,4R)-3-(2-((1-cyclopropyl-1H-pyrazol-4-yl) amino)-5-methyl-7H-pyrrolo[2,3-d]pyrimidin-4-yloxy)-4-fluoropiperidin-1-yl)prop-2-en-1-one, 23) 1-(trans-4-fluoro-3-((2-(isoxazol-4-ylamino)-7H-pyrrolo[2,3-d]pyrimidin-4-yl)oxy)piperidin-1-yl)prop-2-en-1-one, 24) 1-((3R,4R)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one, 25) 1-((3S,4S)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one, 26) 1-((3S,4R)-3-((5-chloro-2-((1-ethyl-1H-pyrazol-4-yl) amino)-7H-pyrrolo[2,3-d]pyrimidin-4-yl)oxy)-4-fluoropiperidin-1-yl)prop-2-en-1-one, 27) 1-((3S,4R)-3-((2-((1-ethyl-1H-pyrazol-4-yl)amino)-5-fluoro-7H-pyrrolo[2,3-d]pyrimidin-4-yl)oxy)-4-fluoropiperidin-1-yl)prop-2-en-1-one, 28) 1-((3R,4S)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one, 29) 1-((3R,4S)-4-fluoro-3-((2-(isoxazol-4-yl)amino)-7H-pyrrolo[2,3-d]pyrimidin-4-yl)oxy)piperidin-1-yl)prop-2-en-1-one, 30) 1-((3S,4R)-4-fluoro-3-((2-((1-(2-hydroxyethyl)-1H-pyrazol-4-yl)amino)-7H-pyrrolo[2,3-d]pyrimidin-4-yl) oxy)piperidin-1-yl)prop-2-en-1-one, 31) 1-((3R,4S)-4-fluoro-3-((2-((4-morpholinophenyl) amino)-7H-pyrrolo[2,3-d]pyrimidin-4-yl)oxy)piperidin-1-yl)prop-2-en-1-one, 32) 1-((3R,4S)-4-fluoro-3-((2-((3-methylisothiazol-5-yl) amino)-7H-pyrrolo[2,3-d]pyrimidin-4-yl)oxy)piperidin-1-yl)prop-2-en-1-one, 33) 1-((3R,4S)-4-fluoro-3-((2-((1-(tetrahydro-2H-pyran-4-yl)-1H-pyrazol-4-yl)amino)-7H-pyrrolo[2,3-d]pyrimidin-4-yl)oxy)piperidin-1-yl)prop-2-en-1-one, 34) 1-((3R,4S)-3-((2-(benzo[d]thiazol-6-ylamino)-7H-pyrrolo[2,3-d]pyrimidin-4-yl)oxy)-4-fluoropiperidin-1-yl) prop-2-en-1-one, 35) 1-((3R,4S)-3-((2-((1-cyclopropyl-1H-pyrazol-4-yl) amino)-7H-pyrrolo[2,3-d]pyrimidin-4-yl)oxy)-4-fluoropiperidin-1-yl)prop-2-en-1-one, and 36) 1-((3S,4R)-4-fluoro-3((2-((1-(piperidin-4-yl)-1H-pyrazol-4-yl)amino)-7H-pyrrolo[2,3-d]pyrimidin-4-yl)oxy) piperidin-1-yl)prop-2-en-1-one.

In addition, the compounds of the present disclosure may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1 whose concentration has effective action because it is relatively non-toxic and harmless to the patients and whose side effects do not degrade the beneficial efficacy of the above compound.

Pharmaceutically acceptable salts can be obtained by conventional methods using inorganic or organic acids. For example, the pharmaceutically acceptable salt can be prepared by dissolving the compound represented by Chemical Formula 1 in a water-miscible organic solvent, e.g., acetone, methanol, ethanol or acetonitrile, followed by adding an organic acid or an inorganic acid, and filtering and drying the precipitated crystals. Alternatively, it may be prepared by subjecting a solvent or an excessive amount of acid from the acid-added reaction mixture to reduced pressure and then drying the residue, or by adding a different organic solvent and then filtering the precipitated salt. At this time, the preferred salts may include salts derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palm itic acid, maleic acid, hydroxyrnaleic acid, benzoic acid, hydroxybenzoic acid, phenylacetic acid, cinnamic acid, salicylic acid, methanesulfonic acid, benzenesulfonic acid or toluenesulfonic acid, and the like.

A pharmaceutically unacceptable salt or solvate of the compound of Chemical Formula 1 may be used as an intermediate in the production of the compound of Chemical Formula 1, or the pharmaceutically acceptable salt or the solvate thereof.

The compound of Chemical Formula 1 according to the present disclosure includes not only pharmaceutically acceptable salts thereof, but all solvates and hydrates that can be prepared therefrom, and includes all possible stereoisomers as well. The solvate, the hydrate and the stereoisomer of the compound represented by Chemical Formula 1 may be prepared and used from the compound of Chemical Formula 1 using common methods.

In addition, the compound represented by Chemical Formula 1 according to the present disclosure may be prepared either in a crystalline form or in a non-crystalline form, and when the compound represented by Chemical Formula 1 is prepared in a crystalline form, it may be optionally hydrated or solvated. In the present disclosure, the compound represented by Chemical Formula 1 may not only include a stoichiometric hydrate, but include a compound containing various amounts of water. The solvate of the compound represented by Chemical Formula 1 according to the present disclosure includes both stoichiometric solvates and non-stoichiometric solvates.

Furthermore, as an example; the present disclosure can produce the compound represented by Chemical Formula 1 through Reaction Scheme 1 below.

[Reaction Scheme 1]

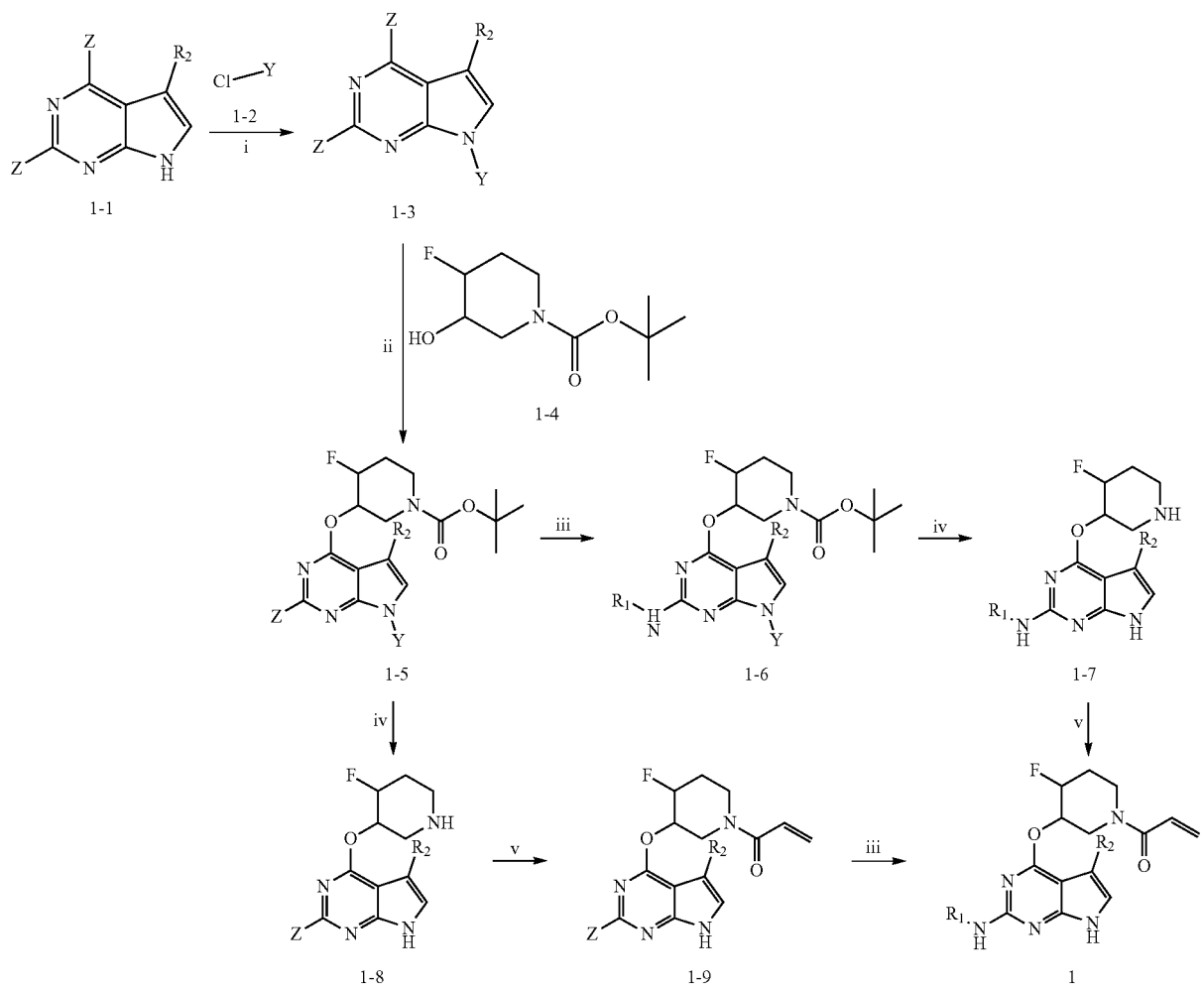

(in Reaction Scheme 1, $R_1$ and $R_2$ are as previously defined, Y is 4-methylbenzylsulfonyl or 2-(trimethylsilyl)ethoxymethyl, Z is halogen, and preferably Z is chloro)

Step i is a step of preparing a compound represented by Chemical Formula 1-3 by reacting a compound represented by Chemical Formula 1-1 with a compound represented by Chemical Formula 1-2. The reaction is preferably carried out at 0° C. or less under basic conditions, and the solvent is preferably acetone, tetrahydrofuran or dimethylformamide.

Step ii is a step of preparing a compound represented by Chemical Formula 1-5 by reacting a compound represented by Chemical Formula 1-3 with a compound represented by Chemical Formula 1-4. The reaction is preferably carried out at 0° C. or less or at room temperature to high temperature in the presence of a base, and the base is preferably sodium hydride, cesium carbonate or diisopropylethylamine. Further, the solvent is preferably tetrahydrofuran, ethanol, and dimethylformamide.

Step iii is a step of preparing a compound represented by Chemical Formula 1-6 by reacting a compound represented by Chemical Formula 1-5 with $R_1$—$NH_2$. The reaction is preferably carried out at 100° C. to 120° C. in the presence of a ligand, a palladium catalyst and a base, or alternatively at a high temperature in the presence of a trifluoroacetic acid, and the solvent is preferably 1,4-dioxane, tert-butanol or 2-butanol.

Step iv is a reaction for removing the protecting group of the compound represented by Chemical Formula 1-6, which is a step for preparing the compound represented by Chemical Formula 1-7. It is preferable to react under acidic conditions (preferably, 6N hydrochloric acid conditions) and then with an aqueous ammonia solution, or alternatively, to react with fluoride, preferably tetrabutylammonium fluoride, under basic conditions, and the solvent is preferably methanol, tetrahydrofuran, or 1,4-dioxane.

Step v is a step of preparing a compound represented by Chemical Formula 1 by reacting a compound represented by Chemical Formula 1-7 with acyl chloride. The reaction is preferably carried out at −20° C. to 0° C. in the presence of triethylamine or sodium hydrogen carbonate. Further, the solvent is preferably a mixture of dichloromethane or tetrahydrofuran and water.

Further, as shown in the Reaction Scheme 1, a compound represented by Chemical Formula 1-5, a compound represented by Chemical Formula 1-8, a compound represented by Chemical Formula 1-9, and a compound represented by Chemical Formula 1 may be prepared in this order, and each step iv, v, and iii is the same as described above, except for the reactants.

According to another embodiment of the present disclosure, there is provided a pharmaceutical composition for preventing or treating diseases which is beneficial for kinase inhibitory actions, comprising the compound represented by Chemical Formula 1, or a pharmaceutically acceptable salt, hydrate, solvate or isomer thereof as an active ingredient.

In this case, the diseases which is associated with kinase inhibitory actions includes inflammatory diseases, autoimmune diseases, proliferative diseases or hyperproliferativ diseases, and immunity mediated diseases, cancers, tumors or the like.

The term "prevention" as used herein refers to any act to delay or inhibit occurrence, spread or recurrence of the above-mentioned diseases by administration of the composition of the present disclosure, and the term "treatment" as used herein refers to any act to improve or change the symptoms of the above diseases for the better by administration of the composition of the present disclosure.

The pharmaceutical composition of the present disclosure can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like, but are not limited thereto. Further, the compounds of the present disclosure can be dissolved in oils, propylene glycol or other solvents commonly used in the preparation of injection solutions. Furthermore, the compounds of the present disclosure can be formulated in ointments or creams for topical application.

Pharmaceutical dosage forms of the compounds of the present disclosure may include using the compounds in the form of pharmaceutically acceptable salts or solvates thereof, and using the compounds alone or as a combination and/or a suitable mixture together with other pharmaceutically active corn pounds.

The compounds of the present disclosure can be formulated into injection solutions by dissolving, suspending or emulsifying the compounds in a water-soluble solvent such as normal saline, 5% dextrose or a non-aqueous solvent such as synthetic fatty acid glyceride, higher fatty acid ester or propylene glycol. Formulations of the present disclosure may include conventional additives such as solubilizers, isotonic agents, suspending agents, emulsifying agents, stabilizers and preservatives.

A preferred dose of the compound of the present disclosure may be varied according to the condition and weight of a patient, the severity of a disease, the type of a drug, and the route and duration of administration, but it may be suitably selected by those skilled in the art. In order to achieve the desirable effects, however, the compound of the present disclosure may be administered daily at a dose of 0.0001 to 100 mg/kg (body weight), and preferably 0.001 to 100 mg/kg (body weight). The administration may be performed once a day or in divided doses each day through an oral or parenteral route. Depending on the method of administration, the composition may contain the compound of the present disclosure in an amount of 0.001 to 99% by weight, preferably 0.01 to 60% by weight.

The pharmaceutical composition according to the present disclosure may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present disclosure or a pharmaceutically acceptable salt, hydrate, solvate or isomer thereof can be usefully used for the prevention or treatment of diseases which are associated with kinase inhibitory actions.

DETAILED DESCRIPTION OF THE EMBODIMENTS

Below, the present disclosure will be described in more detail by way of examples. However, these examples are provided for illustrative purposes only, and should not be construed as limiting the scope of the present disclosure to these examples.

Example 1: Preparation of 1-(trans-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one

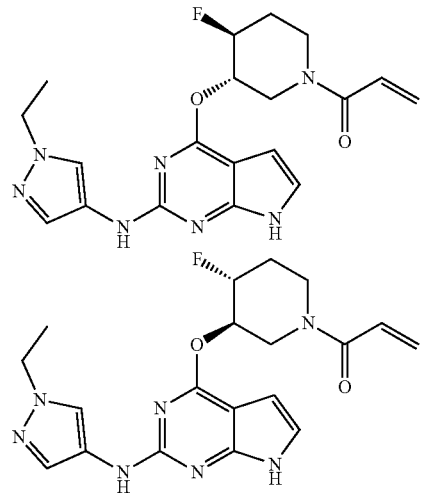

Step 1: Preparation of 2,4-dichloro-7-((2-(trimethylsilyl)ethoxy)methyl)-7H-pyrrolo[2,3-d]pyrimidine After 2,4-dichloro-7H-pyrrolo[2,3-d]pyrimidine (1.0 mol) was dissolved in N,N-dimethylformamide (10.0 mL), sodium hydride (234.0 mg, 5.9 mmol) was added thereto at 0° C., and then stirred for 30 minutes, (2-(Chloromethoxy)ethyl)trimethylsilane (975.0 mg, 5.9 mmol) was added to the reaction mixture, and then stirred at room temperature for 1 hour. After adding ethyl acetate, distilled water was added and the organic layer was separated. The separated organic layer was treated with sodium sulfate, filtered and concentrated under reduced pressure. The residue was separated by column chromatography to obtain 1.7 g (yield: 100.0%) of the title compound.

1H NMR (500 MHz, CD$_3$OD) δ 7.66-7.65 (m, 1H), 6.73-6.72 (m, 1H), 5.62 (s, 2H), 3.58 (m, 2H), 0.91-0.86 (m, 2H), 0.07 (s, 9H)

Step 2: Preparation of trans-tert-butyl-3-((2-chloro-7-((2-(trimethylsilyl)ethoxy)methyl)-7H-pyrrolo[2,3-d]pyrimidin-4-yl)oxy)-4-fluoropiperidine-1-carboxylate After trans-tert-butyl-4-fluoro-3-hydroxypiperidine-1-carboxylate (826.6 mg, 3.8 mmol) was dissolved in tetrahydrofuran (10.0 mL), sodium hydride (180.9 mg, 4.5 mmol) was added thereto at 0° C., and then stirred for 30 minutes. 2,4-Dichloro-7-((2-(trimethylsilyl)ethoxy)methyl)-7H-pyrrolo[2,3-d]pyrimidine (1.2 g, 3.8 mmol) was added to the reaction mixture, and then stirred at room temperature for 2 hours. After adding ethyl acetate, distilled water was added and the organic layer was separated. The separated organic layer was treated with sodium sulfate, filtered and concentrated under reduced pressure. The residue was separated by column chromatography to obtain 1.6 g (yield: 83.1%) of the title compound.

1H NMR (500 MHz, DMSO-$d_6$) δ 7.59-7.58 (m, 1H), 6.60-6.57 (m, 1H), 5.56-5.50 (m, 2H), 5.17-4.95 (m, 2H), 3.88-3.85 (m, 2H), 3.78-3.50 (m, 4H), 2.10-2.05 (m, 1H), 1.81-1.80 (m, 1H), 1.36-1.10 (m, 9H), 0.82 (m, 2H), 0.06 (s, 9H)

Step 3: Preparation of trans-tert-butyl-3-((2-((1-ethyl-1H-pyrazol-4-yl)amino)-7-((2-(trimethylsilyl)ethoxy)methyl)-7H-pyrrolo[2,3-d]pyrimidin-4-yl)oxy)-4-fluoropiperidine-1-carboxylate Tert-butanol (40.0 mL) was added to trans-tert-butyl-3-((2-chloro-7-((2-(trimethylsilyl)ethoxy)methyl)-7H-pyrrolo[2,3-d]pyrimidin-4-yl)oxy)-4-fluoropiperidine-1-carboxylate (1.4 g, 2.7 mmol) and 1-ethyl-1H-pyrazol-4-amine (333.8 mg, 3.0 mmol). Tris(dibenzylidineacetone)dipalladium (125.0 mg, 0.1 mmol), 2-dicyclohexylphosphino-2′,4′,6′-triisopropylbiphenyl (128.6 mg, 0.3 mmol) and potassium carbonate (754.6 mg, 5.5 mmol) were added thereto, and the mixture was stirred at 150° C. for 2 to 3 hours and then cooled to room temperature. After adding ethyl acetate, distilled water was added and the organic layer was separated. The separated organic layer was treated with sodium sulfate, filtered and concentrated under reduced pressure. The residue was separated by column chromatography to obtain 1.3 g (yield: 83.4%) of the title compound.

1H NMR (500 MHz, CD$_3$OD) δ 8.03 (s, 1H), 7.62 (s, 1H), 6.98 (s, 1H), 6.36-6.35 (m, 1H), 5.55-5.52 (m, 2H), 5.33-5.32 (m, 1H), 5.05-5.00 (m, 1H), 4.38-4.14 (m, 3H), 3.89-3.80 (m, 1H), 3.60-3.44 (m, 4H), 2.22-2.01 (m, 1H), 1.89-1.85 (m, 1H), 1.48-1.10 (m, 12H), 0.95-0.86 (m, 2H), 0.11 (s, 9H)

Step 4: Preparation of trans-N-(1-ethyl-1H-pyrazol-4-yl)-4-((4-fluoropiperidin-3-yl)oxy)-7H-pyrrolo[2,3-d]pyrimidine-2-amine 6N hydrochloric acid solution (10.0 mL) dissolved in methanol was added to trans-tert-butyl-3-((2-((1-ethyl-1H-pyrazol-4-yl)amino)-7-((2-(trimethylsilyl)ethoxy)methyl)-7H-pyrrolo[2,3-d]pyrimidin-4-yl)oxy)-4-fluoropiperidine-1-carboxylate (1.3 g, 2.3 mmol), and the mixture was stirred at room temperature for 2 hours. The reaction product was concentrated, and then 1,4-dioxane (20.0 mL) and ammonia water (10.0 mL) were added to the residue. The reaction mixture was stirred at room temperature for 12 hours and then concentrated to obtain 785.8 mg (yield: 100.0%) of the title compound without further purification. After concentrating the reaction product, 1,4-dioxane (20.0 mL) and ammonia water (10.0 mL) were added to the residue. After stirring at room temperature for 12 hours, the reaction product was concentrated to obtain 785.8 mg (yield: 100.0%) of the title compound without further purification.

Step 5: Preparation of 1-(trans-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one After trans-N-(1-ethyl-1H-pyrazol-4-yl)-4-((4-fluoropiperidin-3-yl)oxy)-7H-pyrrolo[2,3-d]pyrimidine-2-amine (785.8 mg, 2.3 mmol) and sodium bicarbonate (599.8 mg, 6.9 mmol) were dissolved in tetrahydrofuran/distilled water (15.0 m L/3.0 mL), acryloyl chloride (212.7 uL, 2.6 mmol) was added thereto at 0° C. The reaction mixture was stirred at 0° C. for 1 hour. After adding ethyl acetate, distilled water was added and the organic layer was separated. The separated organic layer was treated with sodium sulfate, filtered and concentrated under reduced pressure. The residue was separated by column chromatography to obtain 250.0 mg (yield: 27.5%) of the title compound.

1H NMR (500 MHz, CD$_3$OD) δ 7.98-7.96 (m, 1H), 7.57-7.55 (m, 1H), 6.84-6.53 (m, 2H), 6.26-6.08 (m, 2H), 5.78-5.52 (m, 1H), 5.41-5.40 (m, 1H), 5.10-5.04 (m, 1H), 4.50-4.06 (m, 4H), 3.89-3.86 (m, 1H), 3.55-3.41 (m, 1H), 2.19-2.16 (m, 1H), 1.95-1.93 (m, 1H), 1.45-1.41 (m, 3H)

Example 2: Preparation of 1-(trans-3-((2-((1-(2,2-difluoroethyl)-1H-pyrazol-4-yl)amino)-7H-pyrrolo[2,3-d]pyrimidin-4-yl)oxy)-4-fluoropiperidin-1-yl)prop-2-en-1-one

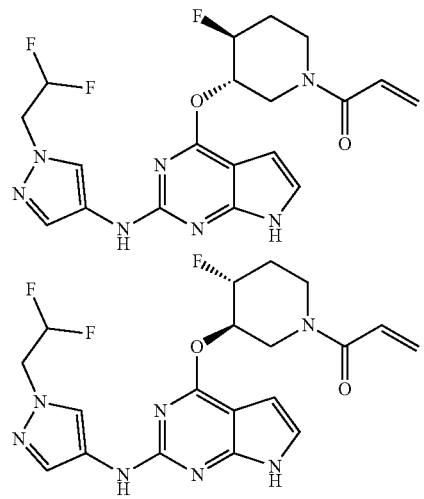

13.9 mg (yield: 35.9%) of the title compound was obtained in the same manner as in Example 1, except that 1-(2,2-difluoroethyl)-1H-pyrazol-4-amine was used instead of 1-ethyl-1H-pyrazol-4-amine in Example 1.

1H NMR (500 MHz, CD$_3$OD) δ 8.13-8.08 (m, 1H), 7.65-7.60 (m, 1H), 6.87-6.54 (m, 2H), 6.28-6.07 (m, 3H), 5.79-5.55 (m, 1H), 5.45-5.44 (m, 1H), 5.05-4.99 (m, 1H), 4.53-4.46 (m, 3H), 4.16-4.13 (m, 1H), 3.92-3.89 (m, 1H), 3.62-3.44 (m, 1H), 2.19-2.17 (m, 1H), 1.97-1.96 (m, 1H)

Example 3: Preparation of 1-(trans-3-((2-(1-cyclopropyl-1H-pyrazol-4-ylamino)-7H-pyrrolo[2,3-d]pyrimidin-4-yloxy)-4-fluoropiperidin-1-yl)prop-2-en-1-one

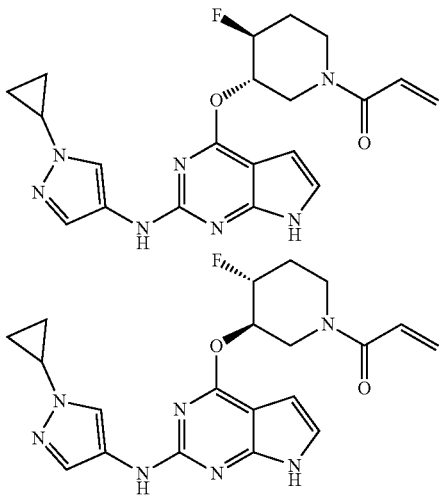

10.9 mg (yield: 42.2%) of the title compound was obtained in the same manner as in Example 1, except that 1-cyclopropyl-1H-pyrazol-4-amine was used instead of 1-ethyl-1H-pyrazol-4-amine in Example 1.

1H NMR (500 MHz, CD$_3$OD) δ 8.03-7.99 (m, 1H), 7.59-7.54 (m, 1H), 6.86-6.56 (m, 2H), 6.27-6.21 (m, 1H), 6.12-6.04 (m, 1H), 5.80-5.53 (m, 1H), 5.44-5.43 (m, 1H), 5.25-5.00 (m, 2H), 4.25-4.12 (m, 2H), 3.92-3.89 (m, 1H), 3.62-3.45 (m, 1H), 2.19-2.18 (m, 1H), 1.95-1.92 (m, 1H), 1.13-1.01 (m, 4H)

Example 4: Preparation of 1-(cis-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one

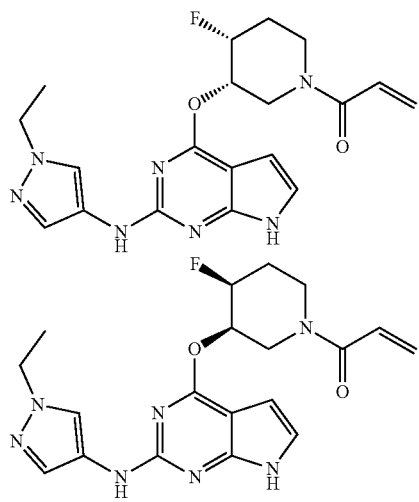

19.3 mg (yield: 27.8%) of the title compound was obtained in the same manner as in Example 1, except that cis-tert-butyl-4-fluoro-3-hydroxypiperidine-1-carboxylate was used instead of trans-tert-butyl-4-fluoro-3-hydroxypiperidine-1-carboxylate in Example 1.

Example 5: Preparation of 1-((3S,4R)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one

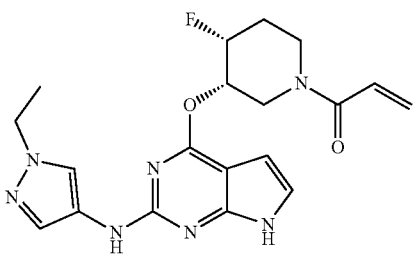 [SMILES: C=CC(=O)N1CC[C@@H](F)[C@@H](Oc2nc(Nc3cnn(CC)c3)nc3[nH]ccc23)C1]

16.2 mg (yield: 57.4%) of the title compound was obtained in the same manner as in Example 1, except that tert-butyl(3S,4R)-4-fluoro-3-hydroxypiperidine-1-carboxylate was used instead of trans-tert-butyl-4-fluoro-3-hydroxypiperidine-1-carboxylate in Example 1.

1H NMR (500 MHz, CD$_3$OD) δ 7.98 (s, 1H), 7.57-7.55 (m, 1H), 6.88-6.45 (m, 2H), 6.30-5.98 (m, 2H), 5.80-5.44 (m, 2H), 5.20-5.05 (m, 1H), 4.40-4.12 (m, 3H), 4.05-3.52 (m, 3H), 2.24-2.21 (m, 1H), 2.01-1.94 (m, 1H), 1.47-1.43 (m, 3H)

Example 6: Preparation of 1-((3S,4R)-3-((2-((1-(2,2-difluoroethyl)-1H-pyrazol-4-yl)amino)-7H-pyrrolo[2,3-d]pyrimidin-4-yl)oxy)-4-fluoropiperidin-1-yl)prop-2-en-1-one

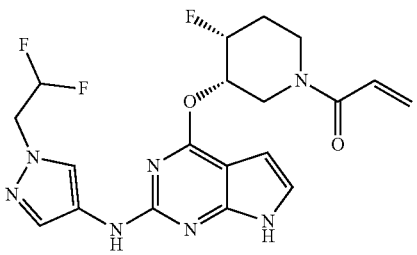 [SMILES: C=CC(=O)N1CC[C@@H](F)[C@@H](Oc2nc(Nc3cnn(CC(F)F)c3)nc3[nH]ccc23)C1]

15.6 mg (yield: 60.2%) of the title compound was obtained in the same manner as in Example 1, except that tert-butyl(3S,4R)-4-fluoro-3-hydroxypiperidine-1-carboxylate was used instead of trans-tert-butyl-4-fluoro-3-hydroxypiperidine-1-carboxylate in Example 1.

1H NMR (500 MHz, CD$_3$OD) δ 8.10-8.07 (m, 1H), 7.65-7.60 (m, 1H), 6.87-6.41 (m, 2H), 6.31-6.21 (m, 2H), 6.14-5.97 (m, 1H), 5.80-5.55 (m, 1H), 5.49-5.43 (m, 1H), 5.15-5.05 (m, 1H), 4.53-4.47 (m, 2H), 4.46-4.20 (m, 1H), 4.10-3.78 (m, 1H), 3.75-3.40 (m, 2H), 2.23-2.20 (m, 1H), 2.01-1.99 (m, 1H)

Example 7: Preparation of 1-((3S,4R)-4-fluoro-3-((2-((3-methylisothiazol-5-yl)amino)-7H-pyrrolo[2,3-d]pyrimidin-4-yl)oxy)piperidin-1-yl)prop-2-en-1-one

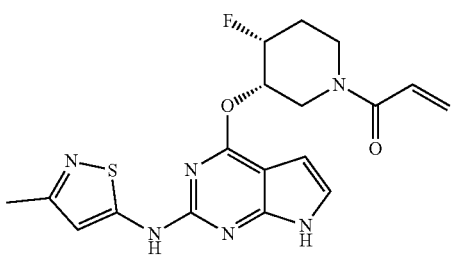

13.5 mg (yield: 53.6%) of the title compound was obtained in the same manner as in Example 1, except that tert-butyl(3S,4R)-4-fluoro-3-hydroxypiperidine-1-carboxylate was used instead of trans-tert-butyl-4-fluoro-3-hydroxypiperidine-1-carboxylate in Example 1.

1H NMR (500 MHz, CD$_3$OD) δ 7.00-6.99 (m, 1H), 6.84-6.45 (m, 2H), 6.39-6.36 (m, 1H), 6.22-5.95 (m, 1H), 5.79-5.41 (m, 2H), 5.20-5.05 (m, 1H), 4.27-4.24 (m, 1H), 4.10-3.98 (m, 1H), 3.83-3.48 (m, 2H), 2.30 (s, 3H), 2.26-2.17 (m, 1H), 2.06-2.01 (m, 1H)

Example 8: Preparation of 1-((3S,4R)-3-((2-((1-cyclopropyl-1H-pyrazol-4-yl)amino)-7H-pyrrolo[2,3-d]pyrimidin-4-yl)oxy)-4-fluoropiperidin-1-yl)prop-2-en-1-one

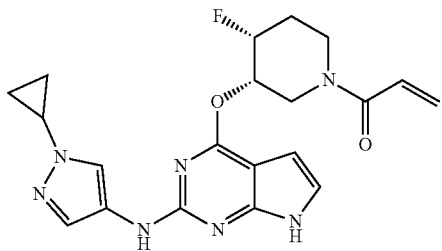 [SMILES: C=CC(=O)N1CC[C@@H](F)[C@@H](Oc2nc(Nc3cnn(C4CC4)c3)nc3[nH]ccc23)C1]

19.0 mg (yield: 51.4%) of the title compound was obtained in the same manner as in Example 1, except that tert-butyl(3S,4R)-4-fluoro-3-hydroxypiperidine-1-carboxylate was used instead of trans-tert-butyl-4-fluoro-3-hydroxypiperidine-1-carboxylate, and 1-cyclopropyl-1H-pyrazol-4-amine was used instead of 1-ethyl-1H-pyrazol-4-amine in Example 1.

1H NMR (500 MHz, CD$_3$OD) δ 8.03-7.99 (m, 1H), 7.59-7.57 (m, 1H), 6.86-6.45 (m, 2H), 6.30-5.98 (m, 3H), 5.79-5.44 (m, 2H), 5.25-5.10 (m, 1H), 4.40-4.15 (m, 1H), 4.05-3.70 (m, 2H), 3.62-3.45 (m, 1H), 2.23-2.20 (m, 1H), 2.02-1.98 (m, 1H), 1.33-1.28 (m, 4H)

Example 9: Preparation of 1-(trans-3-((5-chloro-2-((1-ethyl-1H-pyrazol-4-yl)amino)-7H-pyrrolo[2,3-d]pyrimidin-4-yl)oxy)-4-fluoropiperidin-1-yl)prop-2-en-1-one

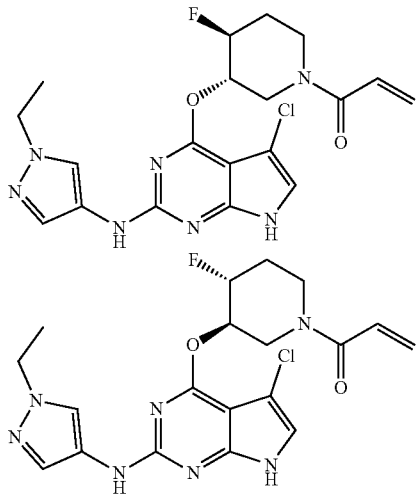

16.0 mg (yield: 46.1%) of the title compound was obtained in the same manner as in Example 1, except that 2,4,5-trichloro-7H-pyrrolo[2,3-d]pyrimidine was used instead of 2,4-dichloro-7H-pyrrolo[2,3-d]pyrimidine in Example 1.

1H NMR (500 MHz, CD$_3$OD) δ 7.99-7.98 (m, 1H), 7.58-7.57 (m, 1H), 6.82-6.52 (m, 2H), 6.19-6.02 (m, 1H), 5.76-5.48 (m, 2H), 5.14-5.05 (m, 1H), 4.29-4.12 (m, 4H), 3.85-3.80 (m, 2H), 2.19-2.17 (m, 1H), 2.01-1.97 (m, 1H), 1.45 (m, 3H)

Example 10: Preparation of 1-(trans-3-((5-chloro-2-((1-cyclopropyl-1H-pyrazol-4-yl)amino)-7H-pyrrolo[2,3-d]pyrimidin-4-yl)oxy)-4-fluoropiperidin-1-yl)prop-2-en-1-one

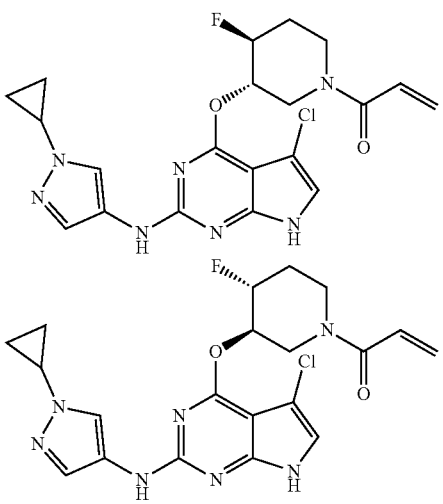

18.0 mg (yield: 30.6%) of the title compound was obtained in the same manner as in Example 1, except that 2,4,5-trichloro-7H-pyrrolo[2,3-d]pyrimidine was used instead of 2,4-dichloro-7H-pyrrolo[2,3-d]pyrimidine, and 1-cyclopropyl-1H-pyrazol-4-amine was used instead of 1-ethyl-1H-pyrazol-4-amine in Example 1.

1H NMR (500 MHz, CD$_3$OD) δ 8.03 (s, 1H), 7.55 (s, 1H), 6.83-6.52 (m, 2H), 6.24-6.15 (m, 1H), 6.06-5.74 (m, 1H), 5.49-5.46 (m, 2H), 5.07-4.98 (m, 1H), 4.31-4.29 (m, 2H), 3.85-3.83 (m, 2H), 2.25-2.17 (m, 1H), 2.02-1.96 (m, 1H), 1.33-1.28 (m, 4H)

Example 11: Preparation of 1-(trans-3-((5-chloro-2-((3-methylisothiazol-5-yl)amino)-7H-pyrrolo[2,3-d]pyrimidin-4-yl)oxy)-4-fluoropiperidin-1-yl)prop-2-en-1-one

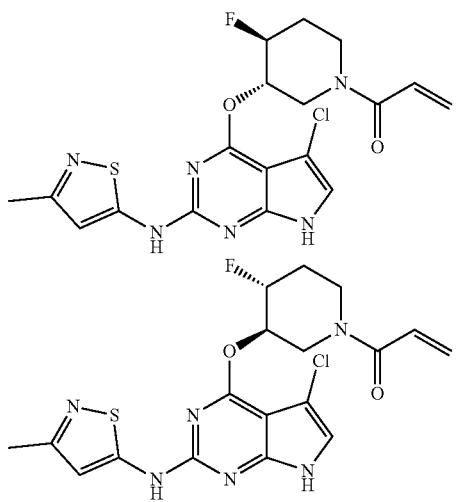

17.2 mg (yield: 51.8%) of the title compound was obtained in the same manner as in Example 1, except that 2,4,5-trichloro-7H-pyrrolo[2,3-d]pyrimidine was used instead of 2,4-dichloro-7H-pyrrolo[2,3-d]pyrimidine, and 3-methylisothiazol-5-amine was used instead of 1-ethyl-1H-pyrazol-4-amine in Example 1.

1H NMR (500 MHz, CD$_3$OD) δ 6.97-6.94 (m, 1H), 6.83-6.54 (m, 2H), 6.17-6.01 (m, 1H), 5.76-5.45 (m, 2H), 5.11-5.02 (m, 1H), 4.35-4.28 (m, 2H), 3.90-3.71 (m, 2H), 2.30-2.19 (m, 4H), 2.01-1.98 (m, 1H)

Example 12: Preparation of 4-((trans-1-acryloyl-4-fluoropiperidin-3-yl)oxy)-2-((1-ethyl-1H-pyrazol-4-yl)amino)-7H-pyrrolo[2,3-d]pyrimidine-5-carbonitrile

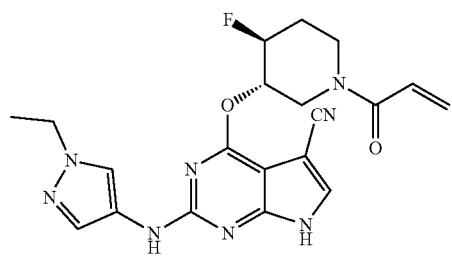

-continued

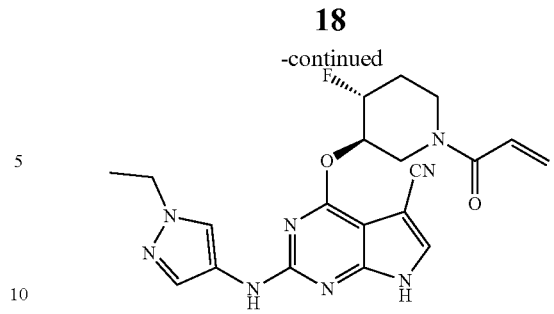

15.4 mg (yield: 60.5%) of the title compound was obtained in the same manner as in Example 1, except that 2,4-dichloro-7H-pyrrolo[2,3-d]pyrimidine-5-carbonitrile was used instead of 2,4-dichloro-7H-pyrrolo[2,3-d]pyrimidine in Example 1.

1H NMR (500 MHz, CD$_3$OD) δ 8.00-7.99 (m, 1H), 7.62-7.60 (m, 2H), 6.83-6.45 (m, 1H), 6.16-6.00 (m, 1H), 5.75-5.40 (m, 2H), 5.15-5.03 (m, 1H), 4.30-4.13 (m, 3H), 3.86-3.40 (m, 3H), 2.19-2.17 (m, 1H), 2.03-1.98 (m, 1H), 1.47-1.44 (m, 3H)

Example 13: Preparation of 4-((trans-1-acryloyl-4-fluoropiperidin-3-yl)oxy)-2-((1-cyclopropyl-1H-pyrazol-4-yl)amino)-7H-pyrrolo[2,3-d]pyrimidine-5-carbonitrile

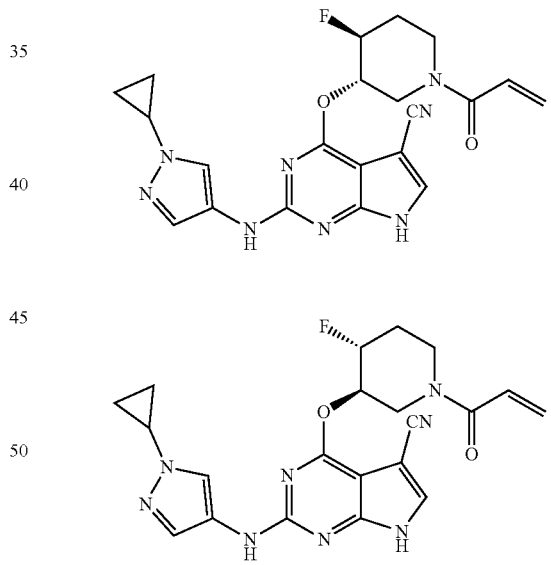

17.1 mg (yield: 52.2%) of the title compound was obtained in the same manner as in Example 1, except that 2,4-dichloro-7H-pyrrolo[2,3-d]pyrimidine-5-carbonitrile was used instead of 2,4-dichloro-7H-pyrrolo[2,3-d]pyrimidine, and 1-cyclopropyl-1H-pyrazol-4-amine was used instead of 1-ethyl-1H-pyrazol-4-amine in Example 1.

1H NMR (500 MHz, CD$_3$OD) δ 8.04 (s, 1H), 7.62-7.57 (m, 2H), 6.84-6.47 (m, 1H), 6.15-5.96 (m, 1H), 5.75-5.40 (m, 2H), 5.13-5.03 (m, 1H), 4.40-3.74 (m, 4H), 3.61-3.59 (m, 1H), 2.19-2.17 (m, 1H), 2.01-1.98 (m, 1H), 1.33-1.30 (m, 4H)

Example 14: Preparation of 4-((trans-1-acryloyl-4-fluoropiperidin-3-yl)oxy)-2-(1-(2,2-difluoroethyl)-1H-pyrazol-4-yl)amino)-7H-pyrrolo[2,3-d]pyrimidine-5-carbonitrile

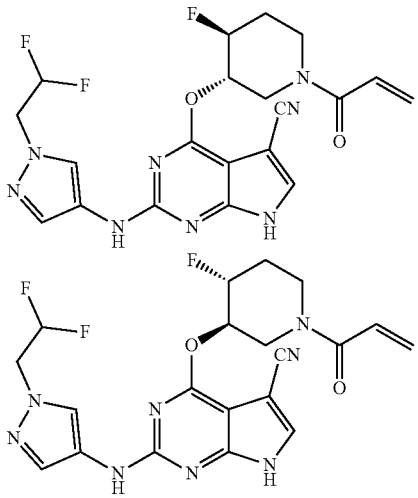

22.8 mg (yield: 92.8%) of the title compound was obtained in the same manner as in Example 1, except that 2,4-dichloro-7H-pyrrolo[2,3-d]pyrimidine-5-carbonitrile was used instead of 2,4-dichloro-7H-pyrrolo[2,3-d]pyrimidine, and 1-(2,2-difluoroethyl)-1H-pyrazol-4-amine was used instead of 1-ethyl-1H-pyrazol-4-amine in Example 1.

1H NMR (500 MHz, CD$_3$OD) δ 8.11 (s, 1H), 7.68-7.61 (m, 2H), 6.83-6.45 (m, 1H), 6.26-5.95 (m, 2H), 5.76-5.39 (m, 2H), 5.10-5.05 (m, 1H), 4.61-4.51 (m, 3H), 4.23-4.20 (m, 1H), 3.90-3.78 (m, 2H), 2.33-2.19 (m, 1H), 2.01-1.97 (m, 1H)

Example 15: Preparation of 1-(cis-3-((2-(1-ethyl-1H-pyrazol-4-yl)amino)-5-fluoro-7H-pyrrolo[2,3-d]pyrimidin-4-yl)oxy)-4-fluoropiperidin-1-yl)prop-2-en-1-one

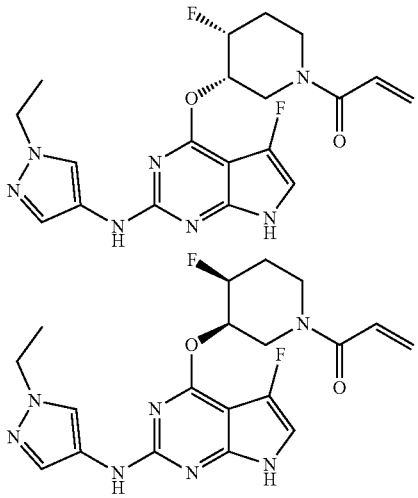

13.5 mg (yield: 28.1%) of the title compound was obtained in the same manner as in Example 1, except that 2,4-dichloro-5-fluoro-7H-pyrrolo[2,3-d]pyrimidine was used instead of 2,4-dichloro-7H-pyrrolo[2,3-d]pyrimidine, and cis-tert-butyl-4-fluoro-3-hydroxypiperidine-1-carboxylate was used instead of trans-tert-butyl-4-fluoro-3-hydroxypiperidine-1-carboxylate in Example 1.

1H NMR (500 MHz, CD$_3$OD) δ 7.98-7.97 (m, 1H), 7.58-7.57 (m, 1H), 6.82-6.41 (m, 2H), 6.18-5.99 (m, 1H), 5.96-5.39 (m, 2H), 5.15-5.03 (m, 1H), 4.32-4.30 (m, 1H), 4.16-4.12 (m, 2H), 3.90-3.62 (m, 2H), 3.22-3.21 (m, 1H), 2.32-2.19 (m, 1H), 2.03-1.98 (m, 1H), 1.47-1.44 (m, 3H)

Example 16: Preparation of 1-(cis-3-((2-((1-(2,2-difluoroethyl)-1H-pyrazol-4-yl)amino)-5-fluoro-7H-pyrrolo[2,3-d]pyrimidin-4-yl)oxy)-4-fluoropiperidin-1-yl)prop-2-en-1-one

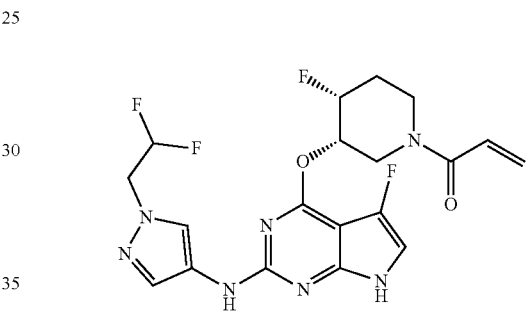

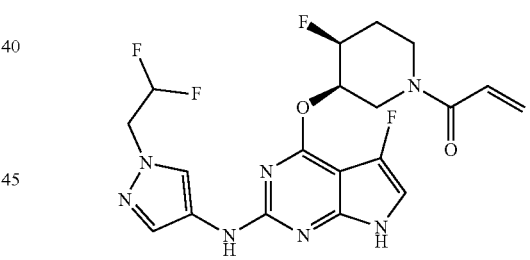

17.4 mg (yield: 40.0%) of the title compound was obtained in the same manner as in Example 1, except that 2,4-dichloro-5-fluoro-7H-pyrrolo[2,3-d]pyrimidine was used instead of 2,4-dichloro-7H-pyrrolo[2,3-d]pyrimidine, cis-tert-butyl-4-fluoro-3-hydroxypiperidine-1-carboxylate was used instead of trans-tert-butyl-4-fluoro-3-hydroxypiperidine-1-carboxylate, and 1-(2,2-difluoroethyl)-1H-pyrazol-4-amine was used instead of 1-ethyl-1H-pyrazol-4-amine in Example 1.

1H NMR (500 MHz, CD$_3$OD) δ 8.08-8.07 (m, 1H), 7.65-7.63 (m, 1H), 6.85-6.40 (m, 2H), 6.18-5.95 (m, 2H), 5.77-5.39 (m, 2H), 5.15-5.03 (m, 1H), 4.54-4.48 (m, 2H), 4.34-4.29 (m, 1H), 3.90-3.80 (m, 1H), 3.64-3.61 (m, 1H), 3.21-3.20 (m, 1H) 2.31-2.19 (m, 1H), 2.03-1.97 (m, 1H)

Example 17: Preparation of 1-(cis-3-((2-(1-ethyl-1H-pyrazol-4-yl)amino)-5-methyl-7H-pyrrolo[2,3-d]pyrimidin-4-yl)oxy)-4-fluoropiperidin-1-yl)prop-2-en-1-one

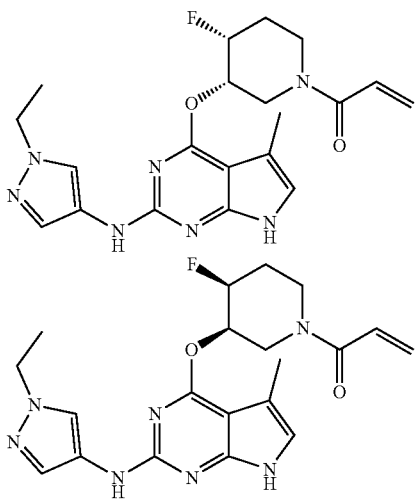

15.4 mg (yield: 33.9%) of the title compound was obtained in the same manner as in Example 1, except that 2,4-dichloro-5-methyl-7H-pyrrolo[2,3-d]pyrimidine was used instead of 2,4-dichloro-7H-pyrrolo[2,3-d]pyrimidine, and cis-tert-butyl-4-fluoro-3-hydroxypiperidine-1-carboxylate was used instead of trans-tert-butyl-4-fluoro-3-hydroxypiperidine-1-carboxylate in Example 1.

1H NMR (500 MHz, CD$_3$OD) δ 7.96 (s, 1H), 7.57-7.54 (m, 1H), 6.89-6.37 (m, 2H), 6.21-5.92 (m, 1H), 5.78-5.36 (m, 2H), 5.14-4.98 (m, 1H), 4.31-4.30 (m, 1H), 4.15-4.08 (m, 3H), 3.65-3.62 (m, 1H), 3.30-3.23 (m, 1H), 2.25-2.18 (m, 4H), 2.02-2.00 (m, 1H), 1.46-1.42 (m, 3H)

Example 18: Preparation of 1-(cis-3-((2-((1-(2,2-difluoroethyl)-1H-pyrazol-4-yl)amino)-5-methyl-7H-pyrrolo[2,3-d]pyrimidin-4-yl)oxy)-4-fluoropiperidin-1-yl)prop-2-en-1-one

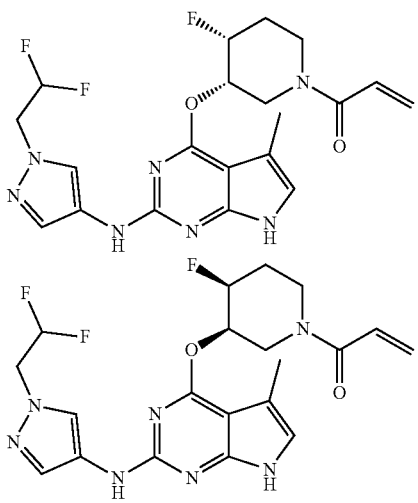

16.4 mg (yield: 32.0%) of the title compound was obtained in the same manner as in Example 1, except that 2,4-dichloro-5-methyl-7H-pyrrolo[2,3-d]pyrimidine was used instead of 2,4-dichloro-7H-pyrrolo[2,3-d]pyrimidine, cis-tert-butyl-4-fluoro-3-hydroxypiperidine-1-carboxylate was used instead of trans-tert-butyl-4-fluoro-3-hydroxypiperidine-1-carboxylate, and 1-(2,2-difluoroethyl)-1H-pyrazol-4-amine was used instead of 1-ethyl-1H-pyrazol-4-amine in Example 1.

1H NMR (500 MHz, CD$_3$OD) δ 8.07-8.06 (m, 1H), 7.64-7.60 (m, 1H), 6.89-6.37 (m, 2H), 6.22-6.14 (m, 1H), 5.94-5.76 (m, 1H), 5.64-5.50 (m, 1H), 5.37-5.35 (m, 1H), 5.15-5.06 (m, 1H), 4.53-4.47 (m, 2H), 4.33-4.30 (m, 1H), 4.05-4.04 (m, 1H), 3.64-3.61 (m, 1H), 3.22-3.21 (m, 1H), 2.25-2.19 (m, 4H), 2.03-1.98 (m, 1H)

Example 19: Preparation of 1-((3S,4R)-3-((2-((1-ethyl-1H-pyrazol-4-yl)amino)-5-methyl-7H-pyrrolo[2,3-d]pyrimidin-4-yl)oxy)-4-fluoropiperidin-1-yl)prop-2-en-1-one

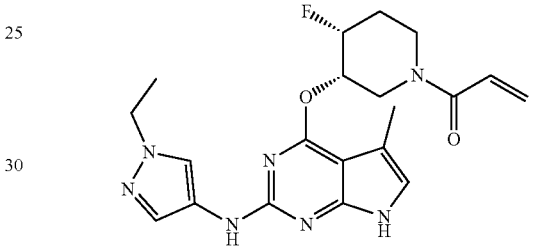

Step 1: Preparation of tert-butyl(3S,4R)-3-((2-chloro-5-methyl-7H-pyrrolo[2,3-d]pyrimidin-4-yl)oxy)-4-fluoropiperidin-1-carboxylate After tert-butyl (3S,4R)-4-fluoro-3-hydroxypiperidine-1-carboxylate (150.0 mg, 0.7 mmol) was dissolved in tetrahydrofuran (3.0 mL), sodium hydride (54.4 mg, 1.4 mmol) was added thereto at 0° C.; and then stirred for 30 minutes. 2,4-Dichloro-5-methyl-7H-pyrrolo[2,3-d]pyrimidine (138.0 mg, 0.7 mmol) was added to the reaction mixture, and then stirred at 80° C. for 12 hours. After adding ethyl acetate, distilled water was added and the organic layer was separated. The separated organic layer was treated with sodium sulfate, filtered and concentrated under reduced pressure. The residue was separated by column chromatography to obtain 124.6 g (yield: 47.3%) of the title compound.

1H NMR (500 MHz, CD$_3$OD) δ 6.94 (s, 1H), 5.56-5.54 (m, 1H), 4.96-4.94 (m, 1H), 4.55-4.52 (m, 1H), 4.12-4.06 (m, 1H), 3.24-2.95 (m, 2H), 2.33 (s, 3H), 2.20-2.16 (m, 1H), 2.01-1.99 (m, 1H), 1.34-1.00 (m, 9H)

Step 2: Preparation of tert-butyl (3S,4R)-3-((2-((1-ethyl-1H-pyrazol-4-yl)amino)-5-methyl-7H-pyrrolo[2,3-d]pyrimidine-4-yl)oxy)-4-fluoropiperidine-1-carboxylate Tert-butanol (2.0 mL) was added to tert-butyl(3S,4R)-3-((2-chloro-5-methyl-7H-pyrrolo[2,3-d]pyrimidin-4-yl)oxy)-4-fluoropiperidin-1-carboxylate (60.0 mg, 0.2 mmol) and 1-ethyl-1H-pyrazol-4-amine (17.8 mg, 0.2 mmol). Tris(dibenzylidineacetone)dipalladium (7.4 mg, 0.01 mmol), 2-dicyclohexylphosphino-2,4,6-triisopropylbiphenyl (7.6 mg, 0.02 mmol) and potassium carbonate (44.2 mg, 0.4 mmol) were added thereto, and the mixture was stirred at 150° C. for 2 to 3 hours and then cooled to room temperature. After adding ethyl acetate, distilled water was added and the organic layer was separated. The separated organic layer was treated with sodium sulfate, filtered and concentrated under reduced pressure. The residue was separated by column chromatography to obtain 24.2 g (yield: 33.9%) of the title compound.

1H NMR (500 MHz, CD₃OD) δ 7.93 (s, 1H), 7.56 (s, 1H), 6.56 (s, 1H), 5.46-5.44 (m, 1H), 4.94-4.92 (m, 1H), 4.67-4.60 (m, 1H), 4.16-4.13 (m, 2H), 3.98-3.70 (m, 1H), 3.15-3.12 (m, 1H), 2.96-2.94 (m, 1H), 2.34 (s, 3H), 2.20-2.17 (m, 1H), 2.00-1.96 (m, 1H), 1.44-1.00 (m, 12H)

Step 3: Preparation of N-(1-ethyl-1H-pyrazol-4-yl)-4-(((3S,4R)-4-fluoropiperidin-3-yl)oxy)-5-methyl-7H-pyrrolo[2,3-d]pyrimidin-2-amine 6N hydrochloric acid solution (2.0 mL) dissolved in methanol was added to tert-butyl (3S,4R)-3-((2-((1-ethyl-1H-pyrazol-4-yl)amino)-5-methyl-7H-pyrrolo[2,3-d]pyrimidine-4-yl)oxy)-4-fluoropiperidine-1-carboxylate (24.2 mg, 0.05 mmol), and the mixture was stirred at room temperature for 2 hours. The reaction product was concentrated to obtain 19.0 mg (yield: 100.0%) of the title compound without further purification.

Step 4: Preparation of 1-((3S,4R)-3-((2-((1-ethyl-1H-pyrazol-4-yl)amino)-5-methyl-7H-pyrrolo[2,3-d]pyrimidin-4-yl)oxy)-4-fluoropiperidin-1-yl)prop-2-en-1-one After N-(1-ethyl-1H-pyrazol-4-yl)-4-(((3S,4R)-4-fluoropiperidin-3-yl)oxy)-5-methyl-7H-pyrrolo[2,3-d]pyrimidin-2-amine (19.0 mg, 0.05 mmol) and sodium bicarbonate (21.0 mg, 0.25 mmol) were dissolved in tetrahydrofuran/distilled water (1.5 mL/0.5 mL), acryloyl chloride (5.0 uL, 0.05 mmol) was added thereto at 0° C. The reaction mixture was stirred at 0° C. for 1 hour. After adding ethyl acetate, distilled water was added and the organic layer was separated. The separated organic layer was treated with sodium sulfate, filtered and concentrated under reduced pressure. The residue was separated by column chromatography to obtain 7.2 g (yield: 33.3%) of the title compound.

1H NMR (500 MHz, CD₃OD) δ 7.97 (s, 1H), 7.56-7.54 (m, 1H), 6.89-6.38 (m, 2H), 6.22-5.92 (m, 1H), 5.79-5.36 (m, 2H), 5.15-4.99 (m, 1H), 4.33-4.29 (m, 1H), 4.16-4.07 (m, 3H), 3.71-3.63 (m, 1H), 3.34-3.21 (m, 1H), 2.25-2.19 (m, 4H), 2.04-2.03 (m, 1H), 1.47-1.43 (m, 3H)

Example 20: Preparation of 1-((3S,4R)-3-((2-((1-(2,2-difluoroethyl)-1H-pyrazol-4-yl)amino)-5-methyl-7H-pyrrolo[2,3-d]pyrimidin-4-yl)oxy)-4-fluoropiperidin-1-yl)prop-2-en-1-one

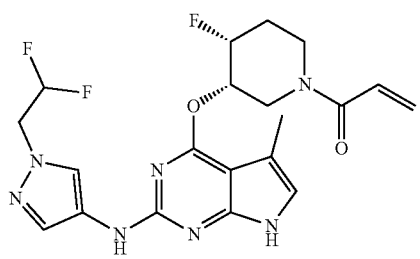 [SMILES: C=CC(=O)N1CC[C@@H](F)[C@@H](Oc2nc(Nc3cnn(CC(F)F)c3)nc3[nH]cc(C)c23)C1]

13.0 mg (yield: 14.1%) of the title compound was obtained in the same manner as in Example 19, except that 1-(2,2-difluoroethyl)-1H-pyrazol-4-amine was used instead of 1-ethyl-1H-pyrazol-4-amine in Example 19.

1H NMR (500 MHz, CD₃OD) δ 8.09-8.01 (m, 1H), 7.69-7.60 (m, 1H), 6.89-6.37 (m, 2H), 6.26-6.14 (m, 1H), 6.03-5.77 (m, 1H), 5.67-5.50 (m, 1H), 5.38-5.33 (m, 1H), 5.15-5.06 (m, 1H), 4.54-4.48 (m, 2H), 4.35-4.32 (m, 1H), 4.07-4.06 (m, 1H), 3.85-3.69 (m, 1H), 3.24-3.16 (m, 1H), 2.28-2.19 (m, 4H), 2.04-2.03 (m, 1H)

Example 21: Preparation of 1-((3S,4R)-4-fluoro-3-((5-methyl-2-((3-methylisothiazol-5-yl)amino)-7H-pyrrolo[2,3-d]pyrimidin-4-yl)oxy)piperidin-1-yl)prop-2-en-1-one

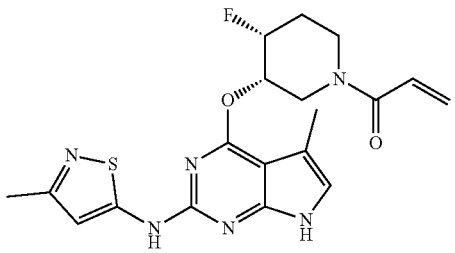 [SMILES: C=CC(=O)N1CC[C@@H](F)[C@@H](Oc2nc(Nc3cc(C)ns3)nc3[nH]cc(C)c23)C1]

16.8 mg (yield: 36.4%) of the title compound was obtained in the same manner as in Example 19, except that 3-methylisothiazol-5-amine was used instead of 1-ethyl-1H-pyrazol-4-amine in Example 19.

1H NMR (500 MHz, CD₃OD) δ 6.89-6.36 (m, 3H), 6.19-5.89 (m, 1H), 5.78-5.32 (m, 2H), 5.34-5.11 (m, 1H), 4.40-4.37 (m, 1H), 3.94-3.86 (m, 1H), 3.70-3.60 (m, 1H), 3.22-3.18 (m, 1H), 2.34 (s, 3H), 2.27-2.19 (m, 4H), 2.07-2.01 (m, 1H)

Example 22: Preparation of 1-((3S,4R)-3-(2-((1-cyclopropyl-1H-pyrazol-4-yl)amino)-5-methyl-7H-pyrrolo[2,3-d]pyrimidin-4-yloxy)-4-fluoropiperidin-1-yl)prop-2-en-1-one

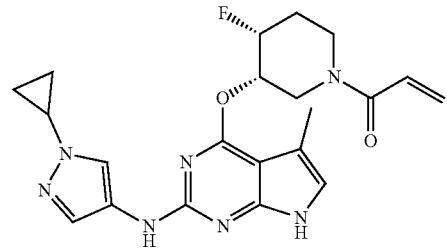 [SMILES: C=CC(=O)N1CC[C@@H](F)[C@@H](Oc2nc(Nc3cnn(C4CC4)c3)nc3[nH]cc(C)c23)C1]

16.8 mg (yield: 36.4%) of the title compound was obtained in the same manner as in Example 19, except that 1-cyclopropyl-1H-pyrazol-4-amine was used instead of 1-ethyl-1H-pyrazol-4-amine in Example 19.

1H NMR (500 MHz, CD₃OD) δ 8.01-8.00 (m, 1H), 7.57-7.53 (m, 1H), 6.88-6.39 (m, 2H), 6.21-5.92 (m, 1H), 5.79-5.37 (m, 2H), 5.15-5.04 (m, 1H), 4.32-4.28 (m, 1H), 4.12-3.89 (m, 1H), 3.70-3.57 (m, 2H), 3.34-3.23 (m, 1H), 2.25-2.15 (m, 4H), 2.06-2.02 (m, 1H), 1.13-1.01 (m, 4H)

Example 23: Preparation of 1-(trans-4-fluoro-3-((2-(isoxazol-4-ylamino)-7H-pyrrolo[2,3-d]pyrimidin-4-yl)oxy)piperidin-1-yl)prop-2-en-1-one

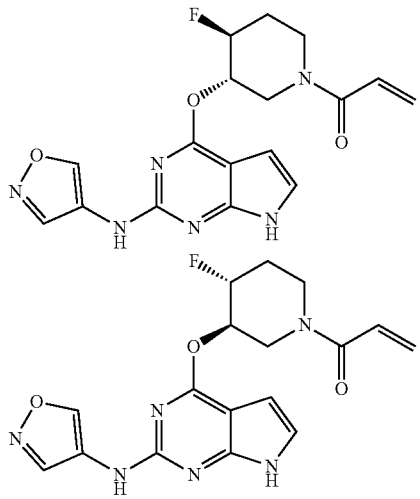

Step 1: Preparation of 2,4-dichloro-7-((2-(trimethylsilyl)ethoxy)methyl)-7H-pyrrolo[2,3-d]pyrimidine After 2,4-dichloro-7H-pyrrolo[2,3-d]pyrimidine (1.0 g, 5.3 mmol) was dissolved in N, N-dimethylformamide (10.0 mL), sodium hydride (234.0 mg, 5.9 mmol) was added thereto at 0° C., and then stirred for 30 minutes. (2-(chloromethoxy)ethyl)trimethylsilane (1.0 g, 5.9 mmol) was added to the reaction mixture and then stirred at room temperature for 1 hour. After adding ethyl acetate, distilled water was added and the organic layer was separated. The separated organic layer was treated with sodium sulfate, filtered and concentrated under reduced pressure. The residue was separated by column chromatography to obtain 1.7 g (yield: 100.0%) of the title corn pound.

1H NMR (500 MHz, CD$_3$OD) δ 7.66-7.65 (m, 1H), 6.73-6.72 (m, 1H), 5.62 (s, 2H), 3.58 (m, 2H), 0.91-0.86 (m, 2H), 0.07 (s, 9H)

Step 2: Preparation of trans-tert-butyl-3-((2-chloro-7-((2-(trimethylsilyl)ethoxy)methyl)-7H-pyrrolo[2,3-d]pyrimidin-4-yl)oxy)-4-fluoropiperidine-1-carboxylate After trans-tert-butyl-4-fluoro-3-hydroxypiperidine-1-carboxylate (826.6 mg, 3.8 mmol) was dissolved in tetrahydrofuran (10.0 mL), sodium hydride (180.9 mg, 4.5 mmol) was added thereto at 0° C. and then stirred for 30 minutes. 2,4-Dichloro-7-((2-(trimethylsilyl)ethoxy)methyl)-7H-pyrrolo[2,3-d]pyrimidine (1.2 g, 3.8 mmol) was added to the reaction mixture and then stirred at room temperature for 2 hours. After adding ethyl acetate, distilled water was added and the organic layer was separated. The separated organic layer was treated with sodium sulfate, filtered and concentrated under reduced pressure. The residue was separated by column chromatography to obtain 1.6 g (yield: 83.1%) of the title compound.

1H NMR (500 MHz, DMSO-d$_6$) δ 7.59-7.58 (m, 1H), 6.60-6.57 (m, 1H), 5.56-5.50 (m, 2H), 5.17-4.95 (m, 2H), 3.88-3.85 (m, 2H), 3.78-3.50 (m, 4H), 2.10-2.05 (m, 1H), 1.81-1.80 (m, 1H), 1.36-1.10 (m, 9H), 0.82-0.81 (m, 2H), 0.06 (s, 9H)

Step 3: Preparation of trans-2-chloro-4-((4-fluoropiperidin-3-yl)oxy)-7H-pyrrolo[2,3-d]pyrimidine 6N hydrochloric acid solution (5.0 mL) dissolved in methanol was added to trans-tert-butyl-3-((2-chloro-7-((2-(trimethylsilyl)ethoxy)methyl)-7H-pyrrolo[2,3-d]pyrimidin-4-yl)oxy)-4-fluoropiperidine-1-carboxylate (260.0 mg, 0.5 mmol), and then the mixture was stirred at room temperature for 2 hours. After concentrating the reaction product, 1,4-dioxane (5.0 mL) and ammonia water (5.0 mL) were added to the residue. After stirring at room temperature for 12 hours, the reaction product was concentrated to obtain 168.5 mg (yield: 100.0%) of the title compound without further purification.

Step 4: Preparation of trans-1-(3-((2-chloro-7H-pyrrolo[2,3-d]pyrimidin-4-yl)oxy)-4-fluoropiperidin-1-yl)prop-2-N-1-one After trans-2-chloro-4-((4-fluoropiperidin-3-yl)oxy)-7H-pyrrolo[2,3-d]pyrimidine (160.0 mg, 0.59 mmol) and sodium bicarbonate (251.6 mg, 2.96 mmol) were dissolved in tetrahydrofuran/distilled water (15.0 mL/5.0 mL), acryloyl chloride (52.5 uL, 0.65 mmol) was added thereto at 0° C. The reaction mixture was stirred at 0° C. for 1 hour. After adding ethyl acetate, distilled water was added and the organic layer was separated. The separated organic layer was treated with sodium sulfate, filtered and concentrated under reduced pressure. The residue was separated by column chromatography to obtain 103.6 g (yield: 54.0%) of the title compound.

1H NMR (500 MHz, CD$_3$OD) δ 7.25-7.24 (m, 1H), 6.80-6.68 (m, 1H), 6.46-6.45 (m, 1H), 6.15-6.11 (m, 1H), 5.78-5.5.59 (m, 1H), 5.54-5.35 (m, 1H), 5.06-4.97 (m, 1H), 4.16-4.10 (m, 1H), 3.93-3.85 (m, 2H), 3.76-3.70 (m, 1H), 2.20-2.15 (m, 1H), 1.98-1.94 (m, 1H)

Step 5: Preparation of 1-(trans-4-fluoro-3-((2-(isoxazol-4-ylamino)-7H-pyrrolo[2,3-d]pyrimidin-4-yl)oxy)piperidin-1-yl)prop-2-en-1-one Trans-1-(3-((2-chloro-7H-pyrrolo[2,3-d]pyrimidin-4-yl)oxy)-4-fluoropiperidin-1-yl)prop-2-N-1-one (17.9 mg, 0.06 mmol) and isooxazyl-4-amine (6.6 mg, 0.06 mmol) were dissolved in 2-butanol (2.0 mL). Trifluoroacetic acid (6.9 uL, 0.07 mmol) was added to the reaction mixture, and reacted at 110° C. for 12 hours, and then the solvent was concentrated. The reaction product was neutralized by adding 7N ammonia solution dissolved in methanol, and the residue was separated by column chromatography to obtain 10.5 mg (yield: 10.2%) of the title compound.

1H NMR (500 MHz, CD$_3$OD) δ 9.12 (s, 1H), 8.51 (s, 1H), 6.92-6.55 (m, 2H), 6.30-6.10 (m, 2H), 5.80-5.50 (m, 1H), 5.45-5.38 (m, 1H), 5.15-4.92 (m, 1H), 4.20-4.10 (m, 1H), 3.95-3.80 (m, 2H), 3.70-3.60 (m, 1H), 3.50-3.40 (m, 1H), 1.65-1.55 (m, 1H)

Example 24: Preparation of 1-((3R,4R)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one

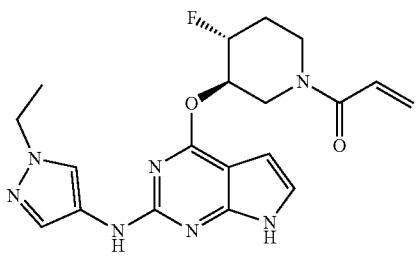 [SMILES: C=CC(=O)N1CC[C@@H](F)[C@H](Oc2nc(Nc3cnn(CC)c3)nc3[nH]ccc23)C1]

The compound of Example 1 was separated by CHIRALCEL OZ-H column to obtain the title compound with an analysis time of 8.4 minutes.

1H NMR (500 MHz, CD$_3$OD) δ 7.98-7.96 (m, 1H), 7.57-7.55 (m, 1H), 6.84-6.53 (m, 2H), 6.26-6.08 (m, 2H), 5.78-5.52 (m, 1H), 5.41-5.40 (m, 1H), 5.10-5.04 (m, 1H), 4.50-4.06 (m, 4H), 3.89-3.86 (m, 1H), 3.55-3.41 (m, 1H), 2.19-2.16 (m, 1H), 1.95-1.93 (m, 1H), 1.45-1.41 (m, 3H)

Example 25: Preparation of 1-((3S,4S)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one

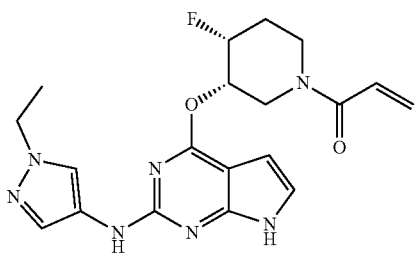 [SMILES: C=CC(=O)N1CC[C@@H](F)[C@@H](Oc2nc(Nc3cnn(CC)c3)nc3[nH]ccc23)C1]

The compound of Example 1 was separated by CHIRALCEL OZ-H column to obtain the title compound with an analysis time of 10.1 minutes.

1H NMR (500 MHz, CD$_3$OD) δ 7.98-7.95 (m, 1H), 7.57-7.55 (m, 1H), 6.84-6.53 (m, 2H), 6.26-6.08 (m, 2H), 5.78-5.52 (m, 1H), 5.41-5.40 (m, 1H), 5.10-5.04 (m, 1H), 4.50-4.06 (m, 4H), 3.89-3.86 (m, 1H), 3.55-3.50 (m, 1H), 2.19-2.16 (m, 1H), 1.95-1.94 (m, 1H), 1.45-1.41 (m, 3H)

Example 26: Preparation of 1-((3S,4R)-3-((5-chloro-2-((1-ethyl-1H-pyrazol-4-yl)amino)-7H-pyrrolo[2,3-d]pyrimidin-4-yl)oxy)-4-fluoropiperidin-1-yl)prop-2-en-1-one

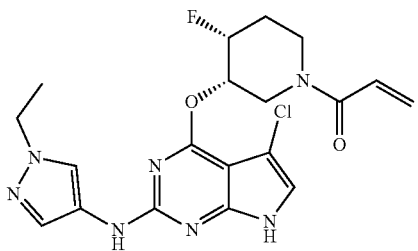 [SMILES: C=CC(=O)N1CC[C@@H](F)[C@@H](Oc2nc(Nc3cnn(CC)c3)nc3[nH]cc(Cl)c23)C1]

12.0 mg (yield: 13.4%) of the title compound was obtained in the same manner as in Example 1, except that 2,4,5-trichloro-7H-pyrrolo[2,3-d]pyrimidine was used instead of 2,4-dichloro-7H-pyrrolo[2,3-d]pyrimidine, and tert-butyl (3S,4R)-4-fluoro-3-hydroxypiperidine-1-carboxylate was used instead of trans-tert-butyl-4-fluoro-3-hydroxypiperidine-1-carboxylate in Example 1.

1H NMR (500 MHz, CD$_3$OD) δ 7.98 (s, 1H), 7.57-7.56 (m, 1H), 6.82-6.40 (m, 2H), 6.18-5.92 (m, 1H), 5.76-5.38 (m, 2H), 5.15-4.95 (m, 1H), 4.38-4.22 (m, 1H), 4.16-4.10 (m, 2H), 3.98-3.72 (m, 1H), 3.65-3.52 (m, 1H), 3.33-3.15 (m, 1H), 2.40-2.10 (m, 1H), 2.09-1.92 (m, 1H), 1.45-1.40 (m, 3H)

Example 27: Preparation of 1-((3S,4R)-3-((2-((1-ethyl-1H-pyrazol-4-yl)amino)-5-fluoro-7H-pyrrolo[2,3-d]pyrimidin-4-yl)oxy)-4-fluoropiperidin-1-yl)prop-2-en-1-one

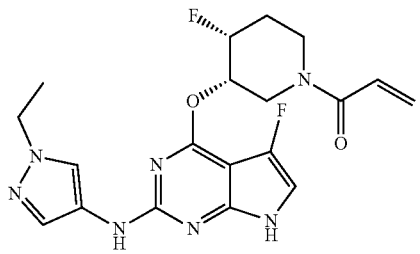

11.6 mg (yield: 20.2%) of the title compound was obtained in the same manner as in Example 1, except that 2,4-dichloro-5-fluoro-7H-pyrrolo[2,3-d]pyrimidine was used instead of 2,4-dichloro-7H-pyrrolo[2,3-d]pyrimidine, and tert-butyl (3S,4R)-4-fluoro-3-hydroxypiperidine-1-carboxylate was used instead of trans-tert-butyl-4-fluoro-3-hydroxypiperidine-1-carboxylate in Example 1.

1H NMR (500 MHz, CD$_3$OD) δ 8.00 (s, 1H), 7.82-7.48 (m, 2H), 6.85-6.60 (m, 1H), 6.20-6.03 (m, 1H), 5.80-5.60 (m, 1H), 5.50-5.35 (m, 1H), 5.20-5.00 (m, 1H), 4.20-4.10 (m, 2H), 4.09-3.60 (m, 4H), 2.33-2.20 (m, 1H), 2.00-1.88 (m, 1H), 1.45-1.38 (m, 3H)

Example 28: Preparation of 1-((3R,4S)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one

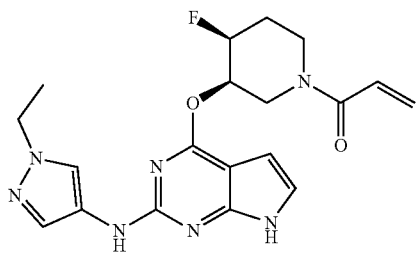 [SMILES: C=CC(=O)N1CC[C@H](F)[C@H](Oc2nc(Nc3cnn(CC)c3)nc3[nH]ccc23)C1]

Step 1: Preparation of 2,4-dichloro-7-((2-(trimethylsilyl)ethoxy)methyl)-7H-pyrrolo[2,3-d]pyrimidine After 2,4-dichloro-7H-pyrrolo[2,3-d]pyrimidine (1.0 g, 5.3 mmol) was dissolved in N,N-dimethylformamide (10.0 mL), sodium hydride (234.0 mg, 5.9 mmol) was added thereto at 0° C. and then stirred for 30 minutes. (2-(Chloromethoxy)ethyl)trimethylsilane (1.0 g, 5.9 mmol) was added to the reaction mixture and then stirred at room temperature for 1 hour. After adding ethyl acetate, distilled water was added and the organic layer was separated. The separated organic layer was treated with sodium sulfate, filtered and concentrated under reduced pressure. The residue was separated by column chromatography to obtain 1.7 g (yield: 100.0%) of the title corn pound.

1H NMR (500 MHz, CD$_3$OD) δ 7.66-7.65 (m, 1H), 6.73-6.72 (m, 1H), 5.62 (s, 2H), 3.58 (m, 2H), 0.91-0.86 (m, 2H), 0.07 (s, 9H)

Step 2: Preparation of tert-butyl (3R,4S)-3-((2-chloro-7-((2-(trimethylsilyl)ethoxy)methyl)-7H-pyrrolo[2,3-d]pyrimidin-4-yl)oxy)-4-fluoropiperidine-1-carboxylate After tert-butyl (3R,4S)-4-fluoro-3-hydroxypiperidine-1-carboxylate (0.7 g, 3.1 mmol) and 2,4-dichloro-7-((2-(trimethylsilyl)ethoxy)methyl)-7H-pyrrolo[2,3-d]pyrimidine (1.0 g, 3.1 mmol) were dissolved in tetrahydrofuran (20.0 mL), cesium carbonate (2.1 g, 6.3 mmol) was added thereto at 0° C. The mixture was stirred at 110° C. for 12 hours. After adding ethyl acetate to the reaction mixture, distilled water was added and the organic layer was separated. The separated organic layer was treated with sodium sulfate, filtered and concentrated under reduced pressure. The residue was separated by column chromatography to obtain 0.9 g (yield: 59.6%) of the title compound.

1H NMR (500 MHz, CD$_3$OD) δ 7.38-7.36 (m, 1H), 6.59-6.58 (m, 1H), 5.57-5.46 (m, 3H), 5.13-5.04 (m, 1H), 4.40-4.36 (m, 1H), 4.09-4.02 (m, 1H), 3.59-3.56 (m, 2H), 3.42-3.38 (m, 1H), 3.16-3.13 (m, 1H), 2.20-2.18 (m, 1H), 2.00-1.98 (m, 1H), 1.41-1.07 (m, 9H), 0.90-0.86 (m, 2H), −0.04-0.11 (m, 9H)

Step 3: Preparation of tert-butyl (3R,4S)-3-((2-chloro-7H-pyrrolo[2,3-d]pyrimidin-4-yl)oxy)-4-fluoropiperidine-1-carboxylate After tert-butyl (3R,4S)-3-((2-chloro-7-((2-(trimethylsilyl)ethoxy)methyl)-7H-pyrrolo[2,3-d]pyrimidin-4-yl)oxy)-4-fluoropiperidine-1-carboxylate (935.0 mg, 1.9 mmol) was dissolved in tetrahydrofuran (10.0 mL), 1.0M tetrabutylammonium fluoride (6.6 mL) and ethylenediamine (0.4 mL, 6.6 mmol) were added thereto. The mixture was stirred at 80° C. for 12 hours. After adding ethyl acetate to the reaction mixture, distilled water was added and the organic layer was separated. The separated organic layer was treated with sodium sulfate, filtered and concentrated under reduced pressure. The residue was separated by column chromatography to obtain 346.6 g (yield: 50.1%) of the title compound.

1H NMR (500 MHz, CD$_3$OD) δ 7.24-7.23 (m, 1H), 6.52-6.51 (m, 1H), 5.45-5.43 (m, 1H), 5.03-5.00 (m, 1H), 4.04-4.02 (m, 1H), 3.98-3.96 (m, 1H), 3.41-3.38 (m, 1H), 3.20-3.18 (m, 1H), 2.22-2.20 (m, 1H), 1.98-1.97 (m, 1H), 1.48-1.10 (m, 9H)

Step 4: Preparation of 1-((3R,4S)-3-((2-chloro-7H-pyrrolo[2,3-d]pyrimidin-4-yl)oxy)-4-fluoropiperidin-1-yl)prop-2-en-1-one After 6N hydrochloric acid solution (5.0 mL) was added to tert-butyl (3R,4S)-3-((2-chloro-7H-pyrrolo[2,3-d]pyrimidin-4-yl)oxy)-4-fluoropiperidine-1-carboxylate (346.3 mg, 0.93 mmol), the mixture was stirred at room temperature for 12 hours, and then the reaction product was concentrated. The concentrated residue was dissolved in tetrahydrofuran/distilled water (4.5 mL/1.5 mL), and then sodium bicarbonate (390.6 mg, 4.7 mmol) was added. After stirring for 30 minutes, acryloyl chloride (82.8 uL, 1.02 mmol) was added thereto at 0° C. The reaction mixture was stirred at room temperature for 1 hour. After adding ethyl acetate, distilled water was added and the organic layer was separated. The separated organic layer was treated with sodium sulfate, filtered and concentrated under reduced pressure. The residue was separated by column chromatography to obtain 260.0 g (yield: 86.2%) of the title compound.

1H NMR (500 MHz, CD$_3$OD) δ 7.25-7.24 (m, 1H), 6.85-6.61 (m, 1H), 6.49-6.48 (m, 1H), 6.16-6.04 (m, 1H), 5.76-5.52 (m, 2H), 5.15-5.05 (m, 1H), 4.16-3.85 (m, 3H), 3.66-3.63 (m, 1H), 2.21-2.18 (m, 1H), 2.05-1.98 (m, 1H)

Step 5: Preparation of 1-((3R,4S)-3-((2-((1-ethyl-1H-pyrazol-4-yl)amino)-7H-pyrrolo[2,3-d]pyrimidin-4-yl)oxy)-4-fluoropiperidin-1-yl)prop-2-en-1-one Tert-butanol (40.0 mL) was added to 1-((3R,4S)-3-((2-chloro-7H-pyrrolo[2,3-d]pyrimidin-4-yl)oxy)-4-fluoropiperidin-1-yl)prop-2-en-1-one (40.0 mg, 0.12 mmol) and 1-ethyl-1H-pyrazol-4-amine (14.4 mg, 0.13 mmol). Tris(dibenzylidineacetone)dipalladium (5.6 mg, 0.01 mmol), 2-dicyclohexylphosphino-2′,4′,6′-triisopropylbiphenyl (5.9 mg, 0.01 mmol) and potassium carbonate (34.0 mg, 0.25 mmol) were added thereto, and the mixture was stirred at 150° C. for 2 to 3 hours and then cooled to room temperature. After adding ethyl acetate, distilled water was added and the organic layer was separated. The separated organic layer was treated with sodium sulfate, filtered and concentrated under reduced pressure. The residue was separated by column chromatography to obtain 36.8 mg (yield: 74.7%) of the title compound.

1H NMR (500 MHz, CD$_3$OD) δ 7.97 (s, 1H), 7.57-7.54 (m, 1H), 6.85-6.43 (m, 2H), 6.35-6.28 (m, 1H), 6.27-5.94 (m, 1H), 5.80-5.35 (m, 2H), 5.20-5.00 (m, 1H), 4.40-3.92 (m, 3H), 3.85-3.60 (m, 2H), 3.54-3.50 (m, 1H), 2.30-2.15 (m, 1H), 2.04-1.90 (m, 1H), 1.50-1.40 (m, 3H)

Example 29: Preparation of 1-((3R,4S)-4-fluoro-3-((2-(isoxazol-4-yl)amino)-7H-pyrrolo[2,3-d]pyrimidin-4-yl)oxy)piperidin-1-yl)prop-2-en-1-one

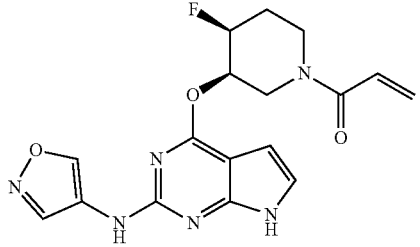 [SMILES: C=CC(=O)N1CC[C@H](F)[C@H](Oc2nc(Nc3cnoc3)nc3[nH]ccc23)C1]

12.0 mg (yield: 5.8%) of the title compound was obtained in the same manner as in Example 23, except that tert-butyl (3R,4S)-4-fluoro-3-hydroxypiperidine-1-carboxylate was used instead of trans-tert-butyl-4-fluoro-3-hydroxypiperidine-1-carboxylate in Example 23.

1H NMR (500 MHz, CD₃OD) δ 9.11 (s, 1H), 8.50 (s, 1H), 6.95-6.90 (m, 1H), 6.88-6.40 (m, 1H), 6.35-6.19 (m, 1H), 6.05-5.75 (m, 1H), 5.65-5.40 (m, 1H), 5.20-5.00 (m, 1H), 4.65-4.50 (m, 1H), 4.30-4.00 (m, 1H), 3.85-3.65 (m, 1H), 3.50-3.40 (m, 1H), 2.30-2.15 (m, 1H), 2.10-1.90 (m, 1H), 1.65-1.55 (m, 1H)

Example 30: Preparation of 1-((3S,4R)-4-fluoro-3-((2-((1-(2-hydroxyethyl)-1H-pyrazol-4-yl)amino)-7H-pyrrolo[2,3-d]pyrimidin-4-yl)oxy)piperidin-1-yl)prop-2-en-1-one

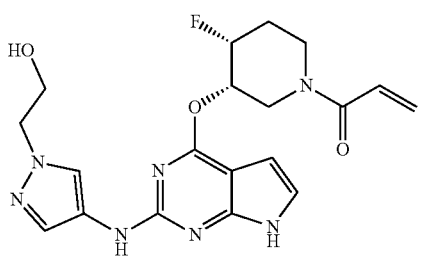

13.7 mg (yield: 53.3%) of the title compound was obtained in the same manner as in Example 28, except that 2-(4-amino-1H-pyrazol-1-yl)ethan-1-ol was used instead of 1-ethyl-1H-pyrazol-4-amine, and tert-butyl (3S,4R)-4-fluoro-3-hydroxypiperidine-1-carboxylate was used instead of tert-butyl (3R,4S)-4-fluoro-3-hydroxypiperidine-1-carboxylate in Example 28.

1H NMR (500 MHz, CD₃OD) δ 8.03-8.02 (m, 1H), 7.59-7.57 (m, 1H), 6.86-6.44 (m, 2H), 6.30-5.97 (m, 2H), 5.80-5.58 (m, 1H), 5.45-5.43 (m, 1H), 5.18 (m, 1H), 4.39-4.04 (m, 4H), 3.89-3.44 (m, 4H), 2.23-2.20 (m, 1H), 2.03-1.97 (m, 1H)

Example 31: Preparation of 1-((3R,4S)-4-fluoro-3-((2-((4-morpholinophenyl)amino)-7H-pyrrolo[2,3-d]pyrimidin-4-yl)oxy)piperidin-1-yl)prop-2-en-1-one

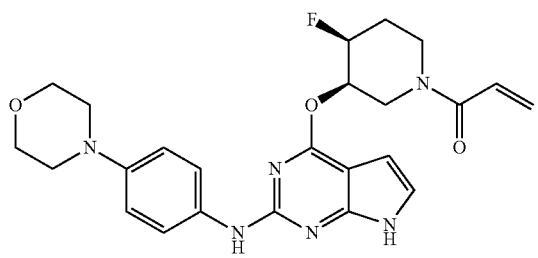 [SMILES: C=CC(=O)N1CC[C@H](F)[C@H](Oc2nc(Nc3ccc(N4CCOCC4)cc3)nc3[nH]ccc23)C1]

10.0 mg (yield: 34.8%) of the title compound was obtained in the same manner as in Example 28, except that 4-morpholinoaniline was used instead of 1-ethyl-1H-pyrazol-4-amine in Example 28.

1H NMR (500 MHz, CD₃OD) δ 7.56-7.54 (m, 1H), 6.93-6.92 (m, 2H), 6.87-6.42 (m, 2H), 6.31-5.97 (m, 2H), 5.79-5.52 (m, 1H), 5.45-5.42 (m, 1H), 5.12-5.01 (m, 1H), 4.36-3.93 (m, 1H), 3.83-3.81 (m, 5H), 3.75-3.55 (m, 3H), 3.07-3.06 (m, 4H), 2.23-2.18 (m, 1H), 1.98-1.93 (m, 1H)

Example 32: Preparation of 1-((3R,4S)-4-fluoro-3-((2-((3-methylisothiazol-5-yl)amino)-7H-pyrrolo[2,3-d]pyrimidin-4-yl)oxy)piperidin-1-yl)prop-2-en-1-one

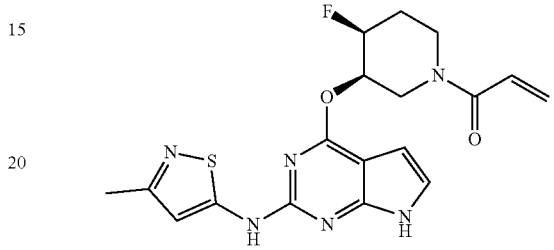

11.2 mg (yield: 45.1%) of the title compound was obtained in the same manner as in Example 28, except that 3-methylisothiazol-5-amine was used instead of 1-ethyl-1H-pyrazol-4-amine in Example 28.

1H NMR (500 MHz, CD₃OD) δ 6.99-6.98 (m, 1H), 6.87-6.44 (m, 2H), 6.38-6.36 (m, 1H), 6.22-5.96 (m, 1H), 5.78-5.70 (m, 1H), 5.56-5.41 (m, 1H), 5.24-5.07 (m, 1H), 4.26-4.23 (m, 1H), 3.95-3.77 (m, 2H), 3.73-3.46 (m, 1H), 2.34 (s, 3H), 2.26-2.22 (m, 1H), 2.07-2.05 (m, 1H)

Example 33: Preparation of 1-((3R,4S)-4-fluoro-3-((2-((1-(tetrahydro-2H-pyran-4-yl)-1H-pyrazol-4-yl)amino)-7H-pyrrolo[2,3-d]pyrimidin-4-yl)oxy)piperidin-1-yl)prop-2-en-1-one

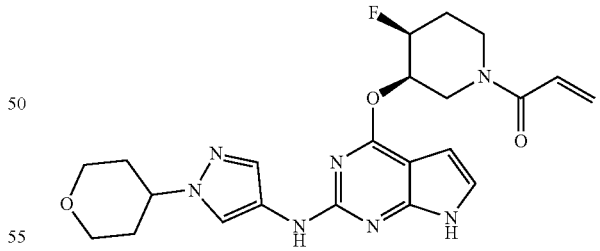

13.0 mg (yield: 46.2%) of the title compound was obtained in the same manner as in Example 28, except that 1-(tetrahydro-2H-pyran-4-yl)-1H-pyrazol-4-amine was used instead of 1-ethyl-1H-pyrazol-4-amine in Example 28.

1H NMR (500 MHz, CD₃OD) δ 8.06-8.05 (m, 1H), 7.60-7.59 (m, 1H), 6.87-6.45 (m, 2H), 6.30-5.98 (m, 2H), 5.79-5.42 (m, 2H), 5.19-5.02 (m, 1H), 4.37-4.31 (m, 1H), 4.16-3.67 (m, 5H), 3.57-3.50 (m, 3H), 2.24-2.17 (m, 1H), 2.11-1.96 (m, 5H).

Example 34: Preparation of 1-((3R,4S)-3-((2-(benzo[d]thiazol-6-ylamino)-7H-pyrrolo[2,3-d]pyrimidin-4-yl)oxy)-4-fluoropiperidin-1-yl)prop-2-en-1-one

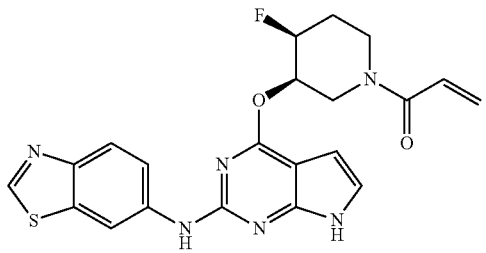 [SMILES: C=CC(=O)N1CC[C@H](F)[C@H](Oc2nc(Nc3ccc4ncsc4c3)nc3[nH]ccc23)C1]

10.3 mg (yield: 38.1%) of the title compound was obtained in the same manner as in Example 28, except that benzo[d]thiazole-6-amine was used instead of 1-ethyl-1H-pyrazol-4-amine in Example 28.

1H NMR (500 MHz, CD$_3$OD) δ 7.92-7.90 (m, 1H), 7.67-7.64 (m, 1H), 6.95-6.94 (m, 1H), 6.88-6.64 (m, 1H), 6.36-6.33 (m, 1H), 6.25-5.95 (m, 1H), 5.81-5.61 (m, 1H), 5.51-5.33 (m, 1H), 5.22-5.06 (m, 1H), 4.39-4.16 (m, 1H), 3.97-3.51 (m, 5H), 2.25-2.17 (m, 1H), 2.01-1.94 (m, 1H)

Example 35: Preparation of 1-((3R,4S)-3-((2-((1-cyclopropyl-1H-pyrazol-4-yl)amino)-7H-pyrrolo[2,3-d]pyrimidin-4-yl)oxy)-4-fluoropiperidin-1-yl)prop-2-en-1-one

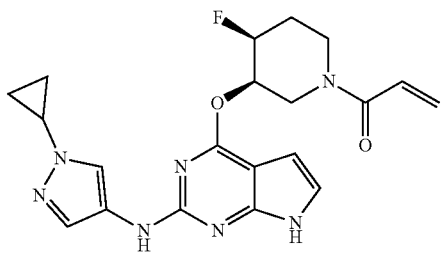 [SMILES: C=CC(=O)N1CC[C@H](F)[C@H](Oc2nc(Nc3cnn(C4CC4)c3)nc3[nH]ccc23)C1]

15.0 mg (yield: 37.4%) of the title compound was obtained in the same manner as in Example 28, except that 1-cyclopropyl-1H-pyrazol-4-amine was used instead of 1-ethyl-1H-pyrazol-4-amine in Example 28.

1H NMR (500 MHz, CD$_3$OD) δ 8.02 (s, 1H), 7.54-7.53 (m, 1H), 6.87-6.45 (m, 2H), 6.30-5.99 (m, 2H), 5.79-5.56 (m, 1H), 5.47-5.33 (m, 1H), 5.20-5.03 (m, 1H), 4.36-4.13 (m, 1H), 3.98-3.53 (m, 4H), 2.23-2.15 (m, 1H), 2.01-1.99 (m, 1H), 1.42-1.23 (m, 4H)

Example 36: Preparation of 1-((3S,4R)-4-fluoro-3-((2-((1-(piperidin-4-yl)-1H-pyrazol-4-yl)amino)-7H-pyrrolo[2,3-d]pyrimidin-4-yl)oxy)piperidin-1-yl)prop-2-en-1-one

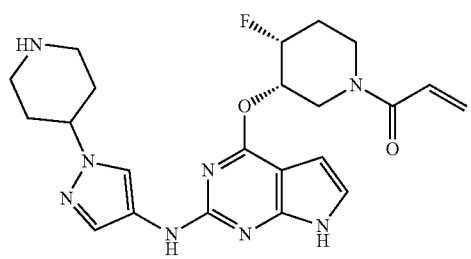 [SMILES: C=CC(=O)N1CC[C@@H](F)[C@@H](Oc2nc(Nc3cnn(C4CCNCC4)c3)nc3[nH]ccc23)C1]

Step 1: Preparation of tert-butyl 4-(4-((4-(((3S,4R)-1-acryloyl-4-fluoropiperidin-3-yl)oxy)-7H-pyrrolo[2,3-d]pyrimidin-2-yl)amino)-1H-pyrazol-1-yl)piperidine-1-carboxylate 424.8 mg (yield: 47.8%) of the title compound was obtained in the same manner as in Example 28, except that tert-butyl 4-(4-amino-1H-pyrazol-1-yl) piperidine-1-carboxylate was used instead of 1-ethyl-1H-pyrazol-4-amine, and tert-butyl (3S,4R)-4-fluoro-3-hydroxypiperidine-1-carboxylate was used instead of tert-butyl (3R,4S)-4-fluoro-3-hydroxypiperidine-1-carboxylate in Example 28.

1H NMR (500 MHz, CD$_3$OD) δ 8.02 (s, 1H), 7.59-7.57 (m, 1H), 6.85-6.40 (m, 2H), 6.30-5.97 (m, 2H), 5.80-5.33 (m, 2H), 5.20-4.94 (m, 1H), 4.38-4.04 (m, 4H), 4.00-3.47 (m, 3H), 3.00-2.80 (m, 2H), 2.28-2.15 (m, 1H), 2.10-2.00 (m, 3H), 1.90-1.80 (m, 2H), 1.46 (m, 9H)

Step 2: Preparation of 1-((3S,4R)-4-fluoro-3-((2-((1-(piperidin-4-yl)-1H-pyrazol-4-yl)amino)-7H-pyrrolo[2,3-d]pyrimidin-4-yl)oxy)piperidin-1-yl)prop-2-en-1-one Trifluoroacetic acid (295.5 uL) was added to tert-butyl 4-(4-((4-(((3S,4R)-1-acryloyl-4-fluoropiperidin-3-yl)oxy)-7H-pyrrolo[2,3-d]pyrimidin-2-yl)amino)-1H-pyrazol-1-yl) piperidine-1-carboxylate (214.0 mg, 0.4 mmol), and the mixture was stirred at room temperature for 4 hours. After concentrating the reaction mixture, ethyl acetate was added, distilled water was added and the organic layer was separated. The separated organic layer was treated with sodium sulfate, filtered and concentrated under reduced pressure to obtain 173.4 g (yield: 98.8%) of the title corn pound.

1H NMR (500 MHz, CD$_3$OD) δ 8.04 (s, 1H), 7.70-7.45 (m, 1H), 6.95-6.40 (m, 2H), 6.38-6.25 (m, 1H), 6.24-5.95 (m, 1H), 5.80-5.35 (m, 2H), 5.20-5.00 (m, 1H), 4.50-4.40 (m, 1H), 4.35-3.90 (m, 2H), 3.85-3.60 (m, 2H), 3.58-3.30 (m, 2H), 3.23-3.10 (m, 2H), 2.35-2.15 (m, 4H), 2.08-1.90 (m, 2H)

Experimental Example 1: Measurement of Inhibitory Activity Against JAK 3 and BTK Enzymes JAK3 and BTK kinases inhibitory activities were measured for the compounds prepared in the Examples through in vitro analysis on the ADP Glow (Glo) platform.

Specifically, the inhibitory activities against JAK3 and BTK kinase were measured using a JAK3 kinase assay kit (Promega, V9441) and a BTK kinase assay kit (Promega, V9071) which were purchased from Promega. Recombinant purified human JAK3 and BTK were diluted with 1×kinase reaction buffer (JAK3: 40 mM Tris-Cl, pH 7.5, 20 mM MgCl$_2$, 0.1 mg/mL BSA and 50 uM DTT/BTK: 40 mM Tris-Cl, pH 7.5, 20 mM MgCl$_2$, 0.1 mg/mL BSA, 2 mM MnCl$_2$ and 50 uM DTT) and added to 96 well plates (JAK3: final concentration of 4 ng per reaction/BTK: final concentration of 8 ng per reaction). The compounds prepared in the previous Examples were treated so as to be finally a 1% DMSO aqueous solution, and a substrate cocktail containing ATP (JAK3: final concentration of 5 uM/BTK: final concentration of 10 uM) and 0.2 ug/uL of Poly(Glu4, Tyr1) peptide (JAK3 and BTK final concentration) in the total 25 uL reactants was added to 96-well plates to initiate enzymatic reaction. After incubation (30° C.) for 1 hour, equivalent volume (25 uL per reaction) of ADP Glo was added and incubated (30° C.) for 40 minutes at room temperature.

Then, a kinase detection reagent (50 uL per reaction) was added and incubated (30° C.) for 30 minutes at room temperature. The kinase activity was measured by chemiluminescence according to the instructions of ADP Glow kinase assay kit, and the inhibitory activity of the compounds according to the present disclosure was calculated. For the analysis of the results of each compound, Microsoft Excel was used, and $IC_{50}$ values were calculated by Sigma-Plot software. The results are shown in Table 1 below. Further, for comparison, Tofacitinib and Ibrutinib were evaluated in a similar way.

TABLE 1

| Example No. | JAK3 $IC_{50}$ (nM) | BTK $IC_{50}$ (nM) |
|---|---|---|
| 1 | 0.3 | 2.4 |
| 2 | 0.3 | 2.5 |
| 3 | 0.3 | 2.5 |
| 4 | 0.4 | 4.2 |
| 5 | 0.2 | 1.5 |
| 6 | 0.2 | 1.5 |
| 7 | 0.2 | 1.3 |
| 8 | 0.2 | 1.4 |
| 9 | 0.3 | 2.1 |
| 10 | 0.4 | 2.8 |
| 11 | 0.3 | 2.5 |
| 12 | 0.2 | 1.3 |
| 13 | 0.3 | 1.1 |
| 14 | 0.2 | 1.0 |
| 15 | 0.7 | 5.9 |
| 16 | 0.6 | 5.9 |
| 17 | 0.7 | 8.6 |
| 18 | 0.7 | 7.0 |
| 19 | 0.4 | 3.4 |
| 20 | 0.4 | 4.5 |
| 21 | 0.2 | 1.5 |
| 22 | 0.4 | 3.6 |
| 23 | 0.7 | 11.6 |
| 24 | 5.9 | ~400 |
| 25 | 0.2 | 1.2 |
| 26 | 0.2 | 2.0 |
| 27 | 2.0 | 2.5 |
| 28 | 15.5 | >400 |
| 29 | 151.7 | >400 |
| 30 | 0.3 | 2.4 |
| 31 | 205.9 | No activity |
| 32 | 83.6 | >400 |
| 33 | 9.0 | >80 |
| 34 | >80 | >400 |
| 35 | 51.9 | — |
| 36 | 0.8 | — |
| Tofacitinib | 3.5 | |
| Ibrutinib | | 0.7 |

Experimental Example 2: JAK3-Mediated Cell Assay (HT-2/IL-2 Assay)

The inhibitory activities against JAK3 kinase at the cellular level were measured for the compounds prepared in the Examples through in vitro analysis of STAT5 phosphorylation induced by IL-2 stimulation in HT-2 cells. Specifically, STAT5 phosphorylation was analyzed using HTRF® phospho-STAT5 (Tyr694) assay kit (Cisbio, 64AT5PEG), which was purchased from Cisbio. HT-2 cells were cultured for 2 hours in growth factor-free medium. The cultured HT-2 cells were dispensed into 96-well plates by 50 ul so as to be a density of $2.5 \times 10^5$ cells/well. The compounds prepared in the previous Examples were prepared so as to be finally a 0.3% DMSO aqueous solution, and HT-2 cells was treated with the compounds for 30 minutes. After the compound treatment, IL-2 was prepared so as to be finally a concentration of 20 ng/ml, and HT-2 cells was treated for 10 minutes. The cells were then disrupted by treating lysis buffers for 30 minutes. The level of STAT5 phosphorylation was measured according to the instructions of HTRF® phospho-STAT5 assay kit, and the inhibitory activity of the compounds according to the invention was calculated. For the analysis of the results of each compound, Microsoft Excel was used, and $IC_{50}$ values were calculated by Sigma-Plot software.

TABLE 2

| Example No. | JAK3 Cell $IC_{50}$ (nM) |
|---|---|
| 1 | 67.4 |
| 4 | 115.2 |
| 5 | 101.0 |
| 9 | 72.3 |
| 11 | 96.0 |
| 25 | 32.3 |

The invention claimed is:

1. A compound represented by Chemical Formula 1:

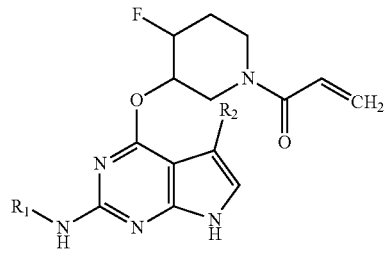

Chemical Formula 1 or a pharmaceutically acceptable salt, stereoisomer, or tautomer thereof,
wherein:
$R_1$ is pyrazolyl, isoxazolyl, isothiazolyl, phenyl, or benzothiazolyl, wherein the pyrazolyl, isoxazolyl, isothiazolyl, phenyl, or benzothiazolyl is optionally substituted with one $R_a$ substituent;
$R_2$ is H, halogen, CN, or $C_{1-5}$ alkyl; and
$R_a$ is $C_{1-5}$ alkyl, $C_{1-5}$ haloalkyl, $C_{1-5}$ hydroxyalkyl, $C_{3-6}$ cycloalkyl, tetrahydropyranyl, piperidinyl, or morpholino.

2. The compound according to claim 1, wherein the compound is represented by Chemical Formula 1-1:

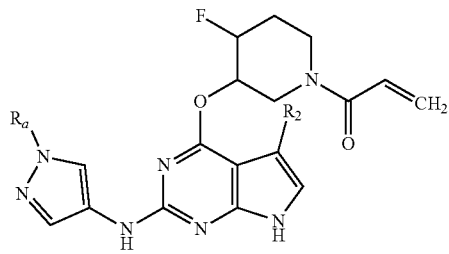

Chemical Formula 1-1 or a pharmaceutically acceptable salt, stereoisomer, or tautomer thereof.

3. The compound according to claim 1, wherein the compound is represented by Chemical Formula 1-2:

Chemical Formula 1-2

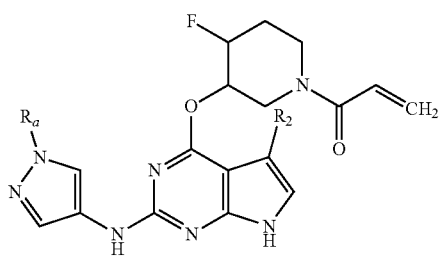

or a pharmaceutically acceptable salt, stereoisomer, or tautomer thereof.

4. The compound according to claim 1, or a pharmaceutically acceptable salt, stereoisomer, or tautomer thereof, wherein $R_2$ is H, F, Cl, Br, CN, $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, $CH_2CH_2CH(CH_3)_2$, or $CH_2C(CH_3)_3$.

5. The compound according to claim 1, or a pharmaceutically acceptable salt, stereoisomer, or tautomer thereof, wherein $R_a$ is $CH_3$, $CH_2F$, $CHF_2$, $CF_3$, $CH_2OH$, $CH_2CH_3$, $CH_2CH_2F$, $CH_2CHF_2$, $CH_2CF_3$, $CH_2CH_2OH$, $CH_2CH_2CH_3$, $CH(CH_3)_2$, $CH_2CH_2CH_2CH_3$, $CH_2CH(CH_3)_2$, $CH_2CH_2CH_2CH_2CH_3$, $CH_2CH_2CH(CH_3)_2$, $CH_2C(CH_3)_3$, cyclopropyl, cyclobutyl, cyclopentyl, cyclohexyl, tetrahydropyranyl, piperidinyl, or morpholino.

6. The compound according to claim 1, or a stereoisomer thereof, wherein the compound, or stereoisomer thereof, is selected from the group consisting of:

(1)
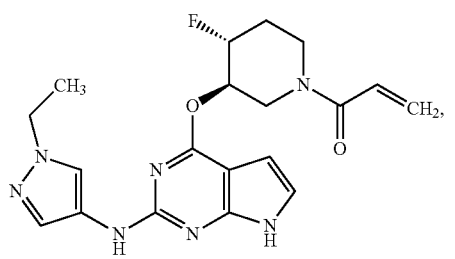

(2)
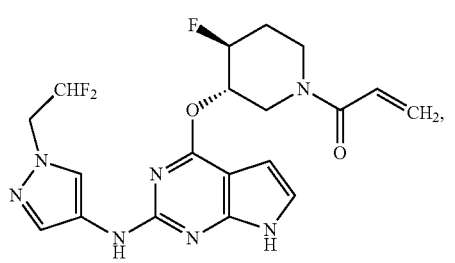

(3)
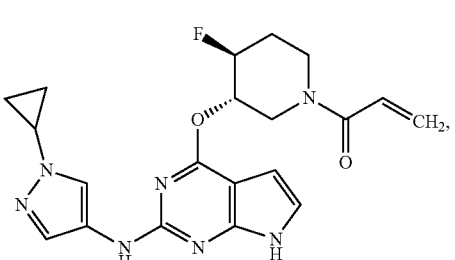

(4)
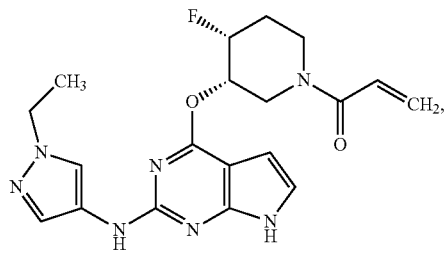

(5)
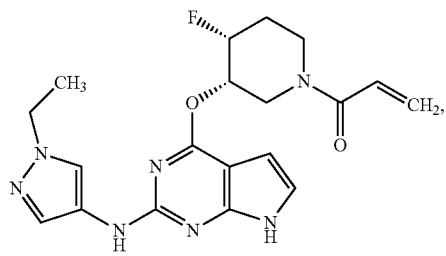

(6)
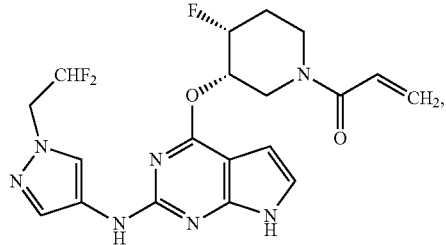

(7)
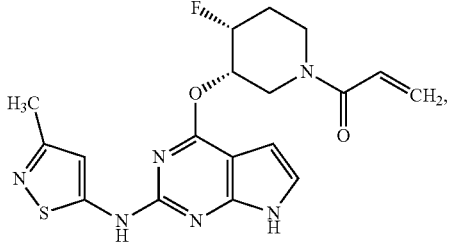

(8)
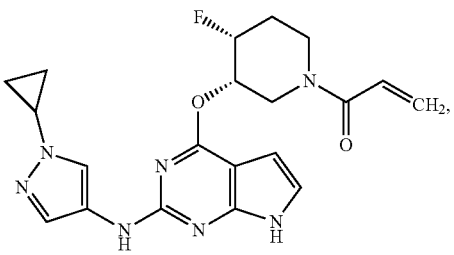

(9)
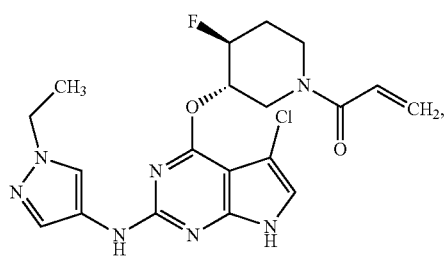

(10)
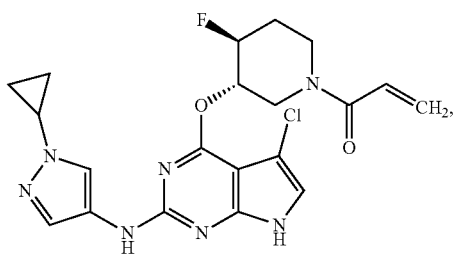
(11)
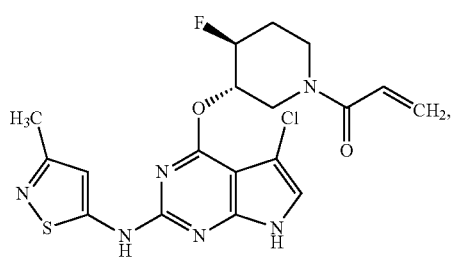
(12)
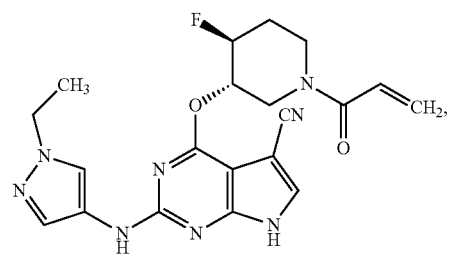
(13)
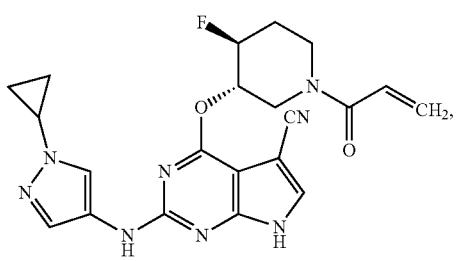
(14)
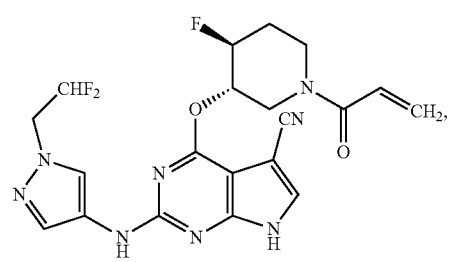
(15)
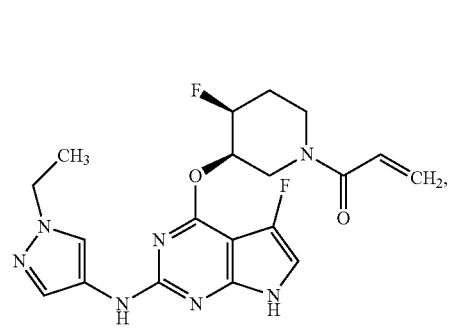
(16)
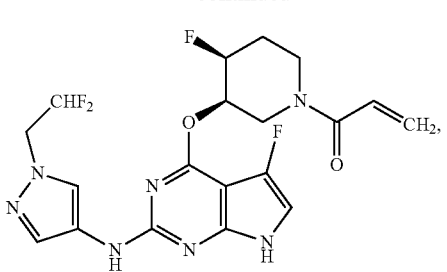
(17)
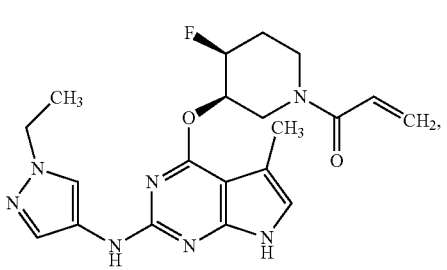
(18)
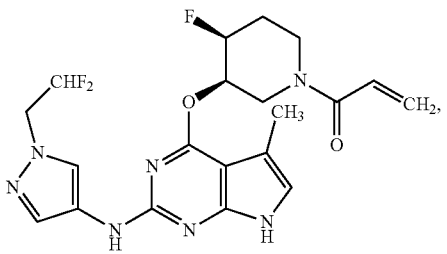
(19)
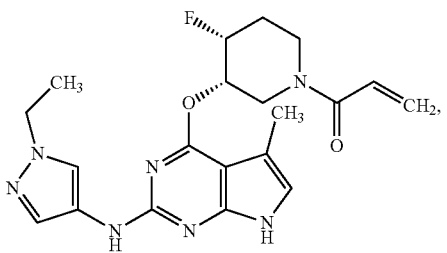
(20)
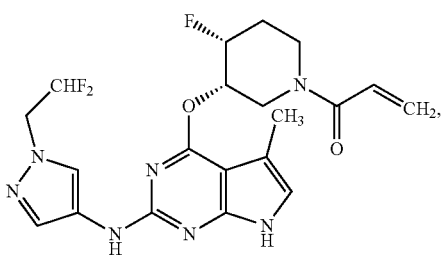
(21)
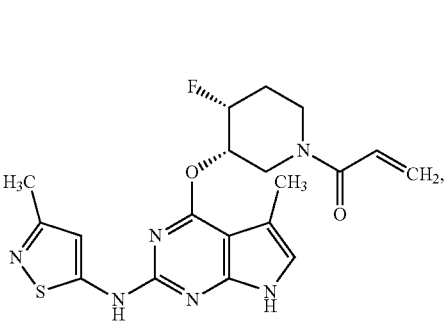

-continued
(22)
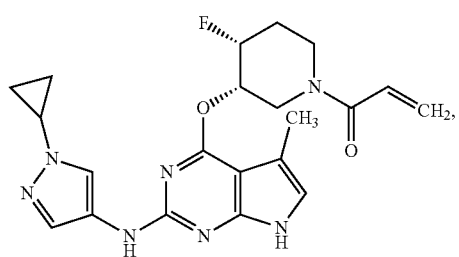
(23)
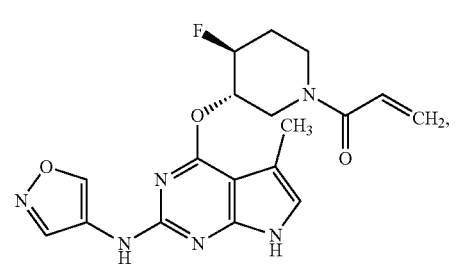
(24)
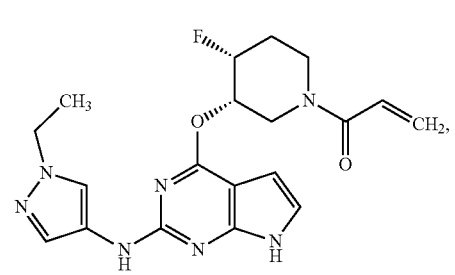
(25)
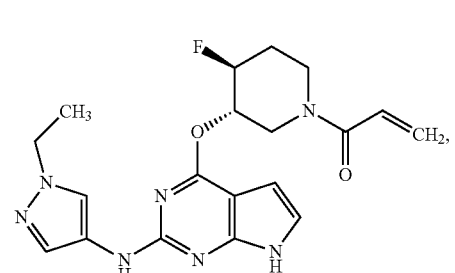
(26)
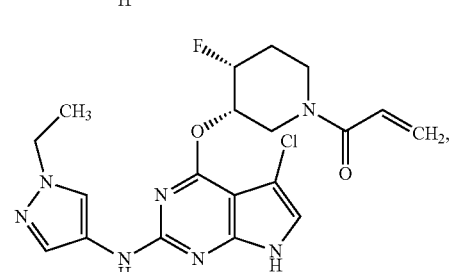
(27)
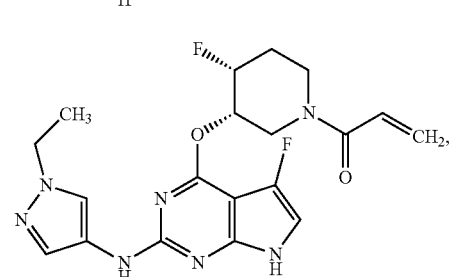
-continued
(28)
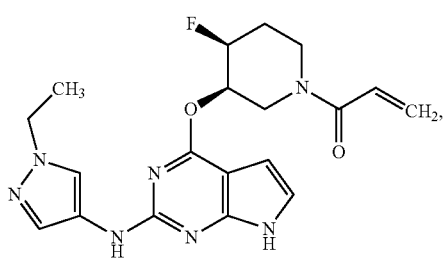
(29)
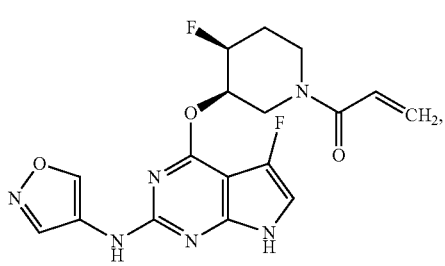
(30)
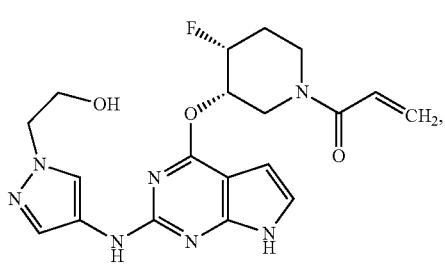
(31)
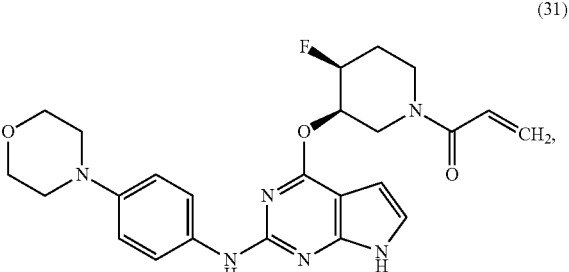
(32)
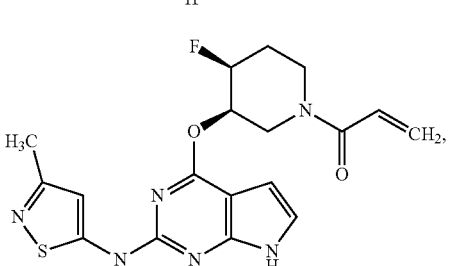
(33)
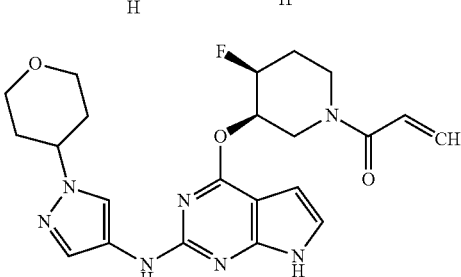

(34)

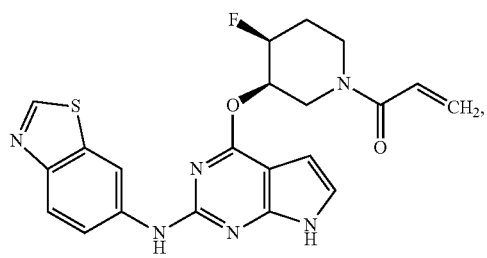

(35)

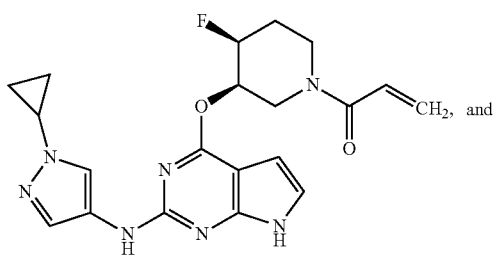

(36)

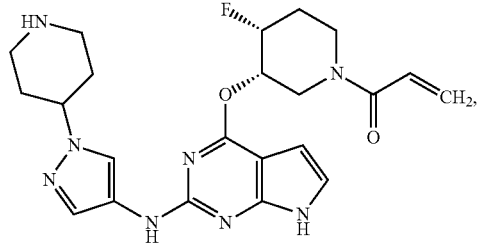

or a pharmaceutically acceptable salt or tautomer thereof.

7. A pharmaceutical composition comprising a pharmaceutically acceptable carrier, adjuvant, or diluent and the compound according to claim 1, or a pharmaceutically acceptable salt, stereoisomer, or tautomer thereof.

8. A method for inhibiting kinase activity in a subject, wherein the method comprises administering to the subject in need thereof an effective amount of the compound according to claim 1, or a pharmaceutically acceptable salt, stereoisomer, or tautomer thereof;
  wherein the kinase is selected from the group consisting of Bruton's tyrosine kinase and Janus kinase 3.

9. The method according to claim 8, wherein the subject has a disease or disorder selected from the group consisting of an autoimmune disease, a cancer, a hyperproliferative disease, an immunity mediated disease, an inflammatory disease, a proliferative disease, and a tumor.

\* \* \* \* \*